US010299749B2

(12) United States Patent
Fukuda et al.

(10) Patent No.: US 10,299,749 B2
(45) Date of Patent: May 28, 2019

(54) MAMMOGRAPHY DEVICE, RADIOGRAPHIC IMAGING METHOD, AND PROGRAM

(71) Applicant: FUJIFILM CORPORATION, Minato-ku, Tokyo (JP)

(72) Inventors: Wataru Fukuda, Kanagawa (JP); Takao Kuwabara, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 460 days.

(21) Appl. No.: 15/080,510

(22) Filed: Mar. 24, 2016

(65) Prior Publication Data

US 2016/0206264 A1    Jul. 21, 2016

Related U.S. Application Data

(63) Continuation of application No. PCT/JP2014/075282, filed on Sep. 24, 2014.

(30) Foreign Application Priority Data

Sep. 27, 2013 (JP) ................. 2013-202061

(51) Int. Cl.
*A61B 6/00* (2006.01)
*A61B 6/02* (2006.01)
(52) U.S. Cl.
CPC .............. *A61B 6/502* (2013.01); *A61B 6/025* (2013.01); *A61B 6/4452* (2013.01);
(Continued)

(58) Field of Classification Search
CPC ....... A61B 6/025; A61B 6/4452; A61B 6/502; A61B 6/5205; A61B 6/5211; A61B 6/545
See application file for complete search history.

(56) References Cited

U.S. PATENT DOCUMENTS

2008/0247509 A1* 10/2008 Kashiwagi ............. A61B 6/502
378/54
2017/0281108 A1* 10/2017 Choi ....................... A61B 6/032

FOREIGN PATENT DOCUMENTS

JP   2005-149762 A   6/2005
JP   2008-253555 A   10/2008
(Continued)

OTHER PUBLICATIONS

English translation of WO 2010/137482 published Dec. 2, 2010.*
(Continued)

*Primary Examiner* — Chih-Cheng Kao
(74) *Attorney, Agent, or Firm* — SOLARIS Intellectual Property Group, PLLC

(57) ABSTRACT

An irradiation condition setting section 52 sets irradiation conditions corresponding to the emission angle of radiation emitted from a radiation source 26. The radiation source 26 emits radiation to a breast at a plurality of different emission angles based on the set irradiation conditions. A radiation detector 36 generates a plurality of projection images corresponding to the plurality of emission angles. An image correction section 56 corrects each projection image such that a difference between at least either contrasts or density values in the plurality of projection images is reduced. A reconstruction unit 58 reconstructs a tomographic image based on the plurality of corrected projection images.

9 Claims, 19 Drawing Sheets

(52) U.S. Cl.
CPC .......... *A61B 6/5205* (2013.01); *A61B 6/5211* (2013.01); *A61B 6/545* (2013.01)

(56) References Cited

FOREIGN PATENT DOCUMENTS

JP        2011-87917 A    5/2011
WO    2010-137482 A1   12/2010

OTHER PUBLICATIONS

International Search Report issued in International Application No. PCT/JP2014/075282 dated Nov. 18, 2014.
Written Opinion of the ISA issued in International Application No. PCT/JP2014/075282 dated Nov. 18, 2014.
Japanese Office Action dated Oct. 4, 2016 in corresponding Japanese Patent Application No. 2015-539260 and a Partial English Translation thereof.

* cited by examiner

MAMMOGRAPHY DEVICE, RADIOGRAPHIC IMAGING METHOD, AND PROGRAM

CROSS-REFERENCE TO RELATED APPLICATIONS

This application is a continuation application of International Application No. PCT/JP2014/075282, filed Sep. 24, 2014, the disclosure of which is incorporated herein by reference in its entirety. Further, this application claims priority from Japanese Patent Application No. 2013-202061 filed Sep. 27, 2013, the disclosure of which is incorporated herein by reference in its entirety.

BACKGROUND OF THE INVENTION

1. Field of the Invention

The present invention relates to a mammography device, a radiographic imaging method, and a program.

2. Description of the Related Art

A radiographic imaging device, such as a mammography device that performs X-ray imaging of the breast for the purpose of early detection of breast cancer or the like, is known. In the mammography device, a device having a tomosynthesis imaging function of generating a tomographic image by reconstructing a plurality of projection images, which are acquired by emitting radiation from a plurality of directions, is known.

JP2005-149762A discloses an X-ray inspection device including an X-ray control unit that controls a tube voltage and a tube current applied to an X-ray tube, an X-ray detector that detects X-rays transmitted through the subject, scanning means for performing a scan in a plurality of directions as transmission directions, and means for generating a sectional image or three-dimensional image of the subject from the transmission data of the subject in the plurality of directions obtained by the X-ray detector. The X-ray inspection device includes means for adjusting the tube voltage so that the transmittance of X-rays in the maximum attenuation path, which is an X-ray path that is the smallest in the transmission of transparent data, becomes a predetermined value.

On the other hand, JP2011-87917A discloses a radiographic imaging apparatus including a radiation source for emitting radiation to the subject, detection means for detecting the radiation transmitted through the subject, body thickness information acquisition means for acquiring the body thickness information of the subject, condition setting means for setting tomographic image acquisition conditions, which indicate a range for acquiring a tomographic image in the subject, based on the body thickness information, and tomographic image acquisition means for acquiring a tomographic image based on the tomographic image acquisition conditions.

SUMMARY OF THE INVENTION

In tomosynthesis imaging for generating a tomographic image using a plurality of projection images acquired by emitting radiation to the subject from a plurality of directions, a distance by which the radiation is transmitted through the subject (hereinafter, referred to as a transmission distance) changes according to the emission angle of radiation. That is, the transmission distance in the case of emitting the radiation from obliquely above the subject is usually longer than the transmission distance in the case of emitting the radiation from directly above the subject. As the transmission distance increases, the attenuation of the radiation in the subject increases, and the SN of the image decreases. In order to avoid the reduction in the SN, increasing the set value of the tube voltage in the radiation source as the transmission distance increases can be considered. However, since the absorption difference of radiation is less likely to be reflected in the image as the set value of the tube voltage increases, the contrast of the image may be reduced.

Here, FIGS. 1A and 1B are density histograms in radiographic images that are captured by setting different tube voltages. A density (gradation) range in FIG. 1A corresponding to the case in which the set value of the tube voltage is relatively large is narrower than a density (gradation) range in FIG. 1B corresponding to the case in which the set value of the tube voltage is relatively small. This indicates that the radiographic image corresponding to FIG. 1A, which is captured by setting the relatively large tube voltage, has low contrast. The density histogram shown in FIG. 1A is located on the lower density side on the whole than in the density histogram shown in FIG. 1B, and the average value of the density value (hereinafter, referred to as an average density value) is different from the density histogram shown in FIG. 1B.

That is, in tomosynthesis imaging, in the case of changing the magnitude of the tube voltage according to the emission angle of radiation, a plurality of projection images having different average density values and contrasts are generated. If the average density values and the contrasts of the plurality of projection images are not the same, the quality of a tomographic image that is reconstructed using the plurality of projection images is reduced.

The present invention has been made in view of the above, and it is an object of the present invention to provide a mammography device, a radiographic imaging method, and a program capable of improving the quality of a tomographic image, which is reconstructed based on a plurality of projection images that are generated by emitting radiation under different conditions for each emission angle, compared to the related art.

According to the present invention, there is provided a mammography device including: a radiation source that emits radiation to a breast at a plurality of different emission angles; a condition setting unit that sets irradiation conditions corresponding to an emission angle of radiation emitted from the radiation source; an image generation unit that generates a plurality of projection images corresponding to the plurality of emission angles by detecting radiation, which is emitted from the radiation source based on the irradiation conditions set by the condition setting unit and is transmitted through the breast; a correction unit that corrects each projection image such that a difference between at least either contrasts or density values in the plurality of projection images is reduced; and a reconstruction unit that reconstructs a tomographic image based on the plurality of projection images corrected by the correction unit.

The condition setting unit may increase a set value of a tube voltage in the radiation source as a transmission distance of radiation transmitted through the breast increases according to the emission angle of radiation.

The correction unit may convert a density value of a projection image corresponding to each of other emission angles such that an area of an overlapping portion between a density histogram in a projection image corresponding to a predetermined emission angle and a density histogram in a projection image corresponding to each of the other emission angles is maximized.

The correction unit may convert a density value of a projection image corresponding to each of other emission angles such that a minimum density value in a projection image corresponding to a predetermined emission angle matches a minimum density value in a projection image corresponding to each of the other emission angles and a maximum density value in the projection image corresponding to the predetermined emission angle matches a maximum density value in the projection image corresponding to each of the other emission angles.

The correction unit may acquire, for each of the plurality of projection images, a first density value when a ratio of the cumulative number of pixels in a case of counting pixels in order of density values to the total number of pixels reaches a first predetermined value and a second density value when the ratio of the cumulative number of pixels in the case of counting pixels in order of density values to the total number of pixels reaches a second predetermined value, and convert a density value of a projection image corresponding to each of other emission angles such that the first density value in a projection image corresponding to a predetermined emission angle matches the first density value in the projection image corresponding to each of the other emission angles and the second density value in a projection image corresponding to the predetermined emission angle matches the second density value in the projection image corresponding to each of the other emission angles.

The correction unit may acquire, for each of the plurality of projection images, a first density value when a ratio of the cumulative number of pixels in a case of counting pixels in order of density values to the total number of pixels reaches a first predetermined value, a second density value when the ratio of the cumulative number of pixels in the case of counting pixels in order of density values to the total number of pixels reaches a second predetermined value, and a third density value of a highest frequency, and convert a density value of a projection image corresponding to each of other emission angles such that differences between the first to third density values in a projection image corresponding to a predetermined emission angle and the first to third density values in the projection image corresponding to each of the other emission angles are reduced.

The correction unit may convert a density value of a projection image corresponding to each of other emission angles such that a density value of a first pixel group including at least one pixel in a projection image corresponding to a predetermined emission angle matches a density value of a pixel group including at least one pixel corresponding to the first pixel group in the projection image corresponding to each of the other emission angles and a density value of a second pixel group including at least one pixel in the projection image corresponding to the predetermined emission angle matches a density value of a pixel group including at least one pixel corresponding to the second pixel group in the projection image corresponding to each of the other emission angles.

The first and second pixel groups may be pixels extracted from different tissues in the breast.

The correction unit may convert a density value of a projection image corresponding to each of other emission angles such that differences between density values of at least three pixel groups in a projection image corresponding to a predetermined emission angle and density values of pixel groups corresponding to the at least three pixel groups in the projection image corresponding to each of the other emission angles are reduced.

The condition setting unit may increase a set value of a tube voltage in the radiation source as a transmission distance of radiation transmitted through the breast increases according to the emission angle of radiation, and the predetermined emission angle may be an emission angle at which the transmission distance of radiation transmitted through the breast is the shortest.

The correction unit may convert a density value of each of the plurality of projection images such that a density value of a first pixel in each of the plurality of projection images matches a first standard density value set for the first pixel and a density value of a second pixel in each of the plurality of projection images matches a second standard density value set for the second pixel.

The correction unit may convert a density value of each pixel in each projection image by linear conversion.

The correction unit may convert image data of each of the plurality of projection images into data in a frequency domain by performing a Fourier transform, and performs filtering processing for multiplying the data in the frequency domain by a filter function of increasing the amount of emphasis in each frequency band as a transmission distance of radiation transmitted through the breast increases according to the emission angle of radiation.

According to the present invention, there is provided a program causing a computer to function as the correction unit in the mammography device described above.

According the present invention, there is provided a radiographic imaging method including: setting irradiation conditions corresponding to an emission angle of radiation emitted from a radiation source; emitting radiation from the radiation source to a breast at a plurality of different emission angles based on the set irradiation conditions; generating a plurality of projection images corresponding to the plurality of emission angles by detecting radiation, which is emitted from the radiation source and is transmitted through the breast; correcting each projection image such that a difference between at least either contrasts or density values in the plurality of projection images is reduced; and reconstructing a tomographic image based on the plurality of the corrected projection images.

According to the present invention, it is possible to improve the quality of a tomographic image, which is reconstructed using a plurality of projection images that are captured under different irradiation conditions, than in the related art.

DESCRIPTION OF THE PREFERRED EMBODIMENTS

Figure 1A:
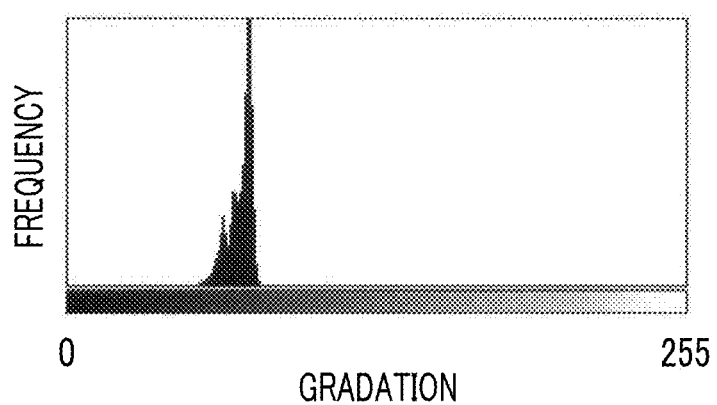
FIG. 1A is a density histogram in a radiographic image.
Figure 1B:
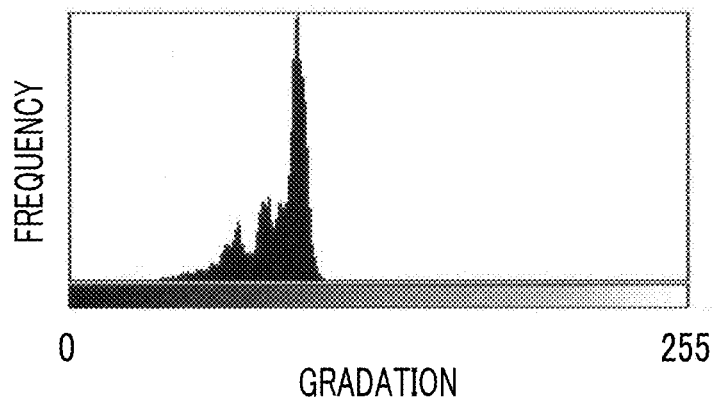
FIG. 1B is a density histogram in a radiographic image.

Hereinafter, a mammography device according to an embodiment of the present invention will be described with reference to the accompanying diagrams. In each of the diagrams, the same reference numerals are given to the same components.

[First Embodiment]

Figure 2:
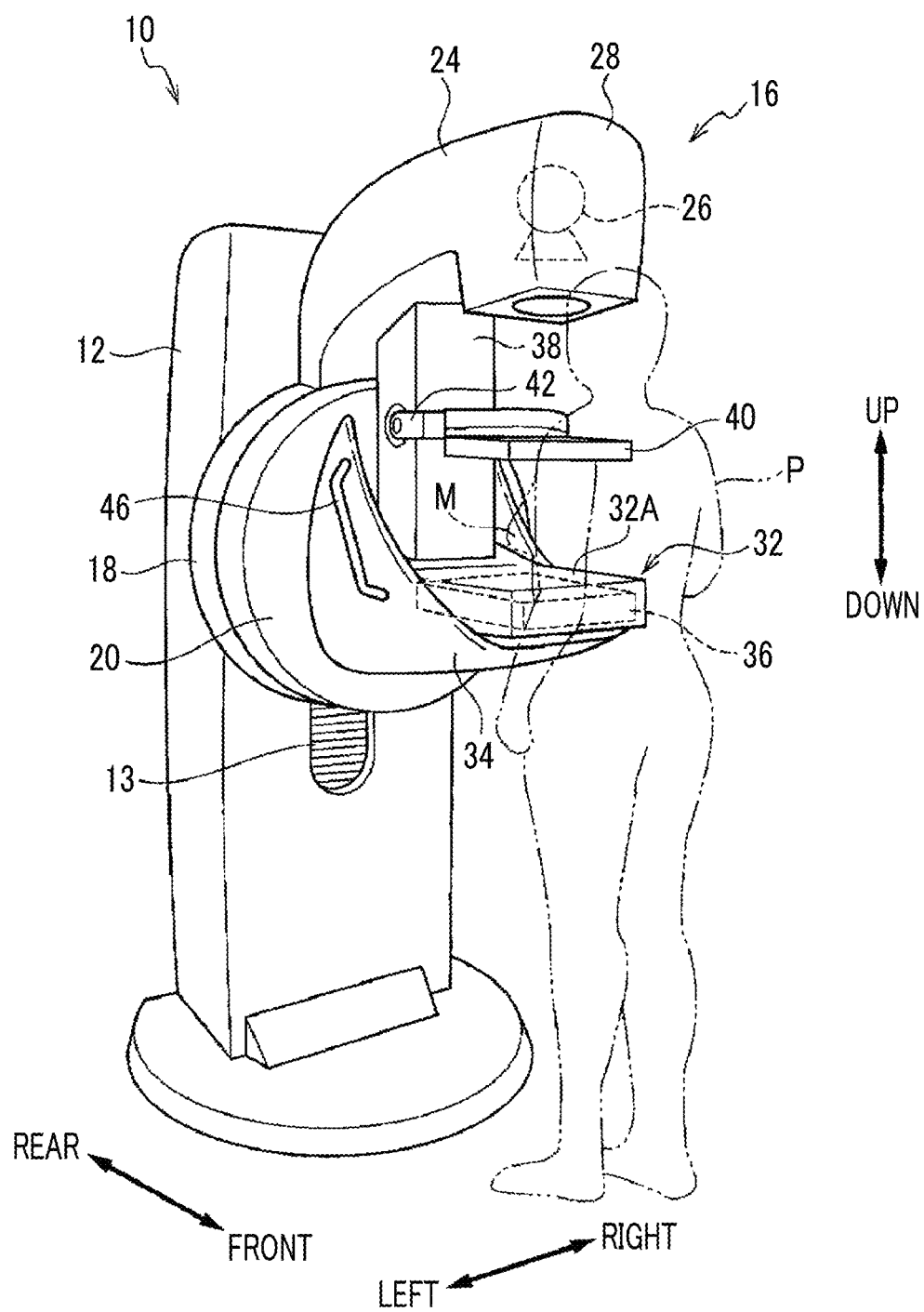
FIG. 2 is a perspective view showing the configuration of a mammography device according to an embodiment of the present invention.
Figure 3:
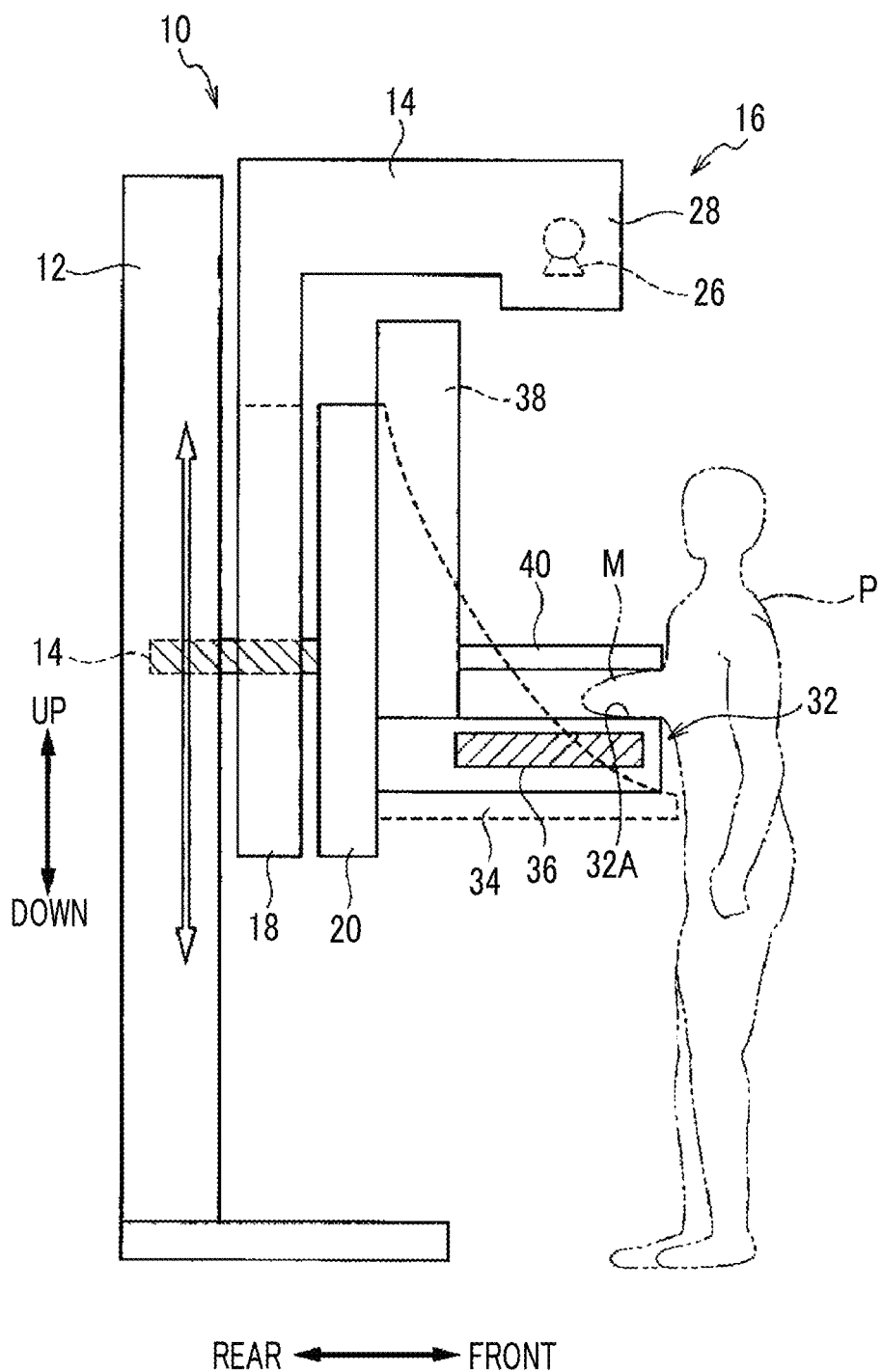
FIG. 3 is a sectional view of the mammography device according to the embodiment of the present invention.

FIG. 2 is a perspective view showing an example of the configuration of a mammography device 10 according to an embodiment of the present invention. FIG. 3 is a sectional view along the centerline in the horizontal direction of the mammography device 10 according to the embodiment of the present invention. In addition, the vertical direction, the horizontal direction, and the front and back direction are directions when viewed from the patient who is a subject P. The mammography device 10 includes a base unit 12, a rotating shaft 14 that is movably provided along a guide unit 13 provided in the base unit 12, and a movable arm unit 16 attached to the rotating shaft 14. The movable arm unit 16 is configured so as to be movable in the vertical direction by the movement of the rotating shaft 14 and be rotatable clockwise and counterclockwise by the rotation of the rotating shaft 14.

The movable arm unit 16 includes a first rotating portion 18 fixed to the rotating shaft 14 and a second rotating portion 20 that is connected to the rotating shaft 14 so as to be able to be disconnected therefrom. The second rotating portion 20 is disposed on the subject P side rather than the first rotating portion 18. The rotating shaft 14 is fixed to the rotation center of the first rotating portion 18, and is connected to the rotation center of the second rotating portion 20. For example, a gear is provided in both of the rotating shaft 14 and the second rotating portion 20. The second rotating portion 20 is connected to the rotating shaft 14 in a state in which the gears are engaged with each other, and is disconnected from the rotating shaft 14 in a state in which the gears are not engaged with each other.

One end of an L-shaped support unit 24 is fixed to the first rotating portion 18. An irradiation unit 28 that emits radiation (X-rays) to a breast M of the subject P is provided on the other end of the support unit 24. The irradiation unit 28 includes a radiation source 26 including an X-ray tube and a radiation source driving section 27 (refer to FIG. 5) that drives the radiation source 26 so as to emit radiation with a tube voltage value, a tube current value, and irradiation time based on the instruction from a main control unit 50 to be described later. The radiation source 26 rotates around the rotating shaft 14 together with the first rotating portion 18 by the rotation of the rotating shaft 14.

A first holding unit 34 for holding an imaging table 32 is attached to the second rotating portion 20. In addition, a handle 46 is provided in the first holding unit 34. The imaging table 32 has an imaging surface 32A in contact with the breast M of the subject P. A radiation detector 36 that detects radiation, which is emitted from the radiation source 26 and is transmitted through the breast M of the subject P, is housed in the imaging table 32.

The radiation detector 36 detects the radiation that is emitted from the radiation source 26 and is transmitted through the breast M, generates and records image data of the radiographic image, and outputs the recorded image data. For example, the radiation detector 36 is configured as a flat panel detector (FPD) having a radiation sensitive layer, a TFT substrate, and the like. The radiation detector 36 reads electric charges, which are generated in the radiation sensitive layer by the emission of radiation and are accumulated in an accumulation portion, using the TFT, converts the electric charges into digital image data showing a radiographic image, and outputs the digital image data.

In addition, a second holding unit 38 for holding a compression plate 40 is attached to the second rotating portion 20. The compression plate 40 is supported so as to be movable in the vertical direction by a support mechanism 42 attached to the second holding unit 38. By the lowering of the compression plate 40, the breast M of the subject P is compressed to be fixed between the imaging surface 32A and the compression plate 40.

The radiation detector 36 housed in the imaging table 32 rotates around the rotating shaft 14 together with the second rotating portion 20, in a state in which the rotating shaft 14 and the second rotating portion 20 are connected to each other, by the rotation of the rotating shaft 14. On the other hand, in a state in which the rotating shaft 14 and the second rotating portion 20 are disconnected from each other, the second rotating portion 20 does not rotate even if the rotating shaft 14 rotates. Accordingly, the imaging table 32 and the radiation detector 36 do not rotate either. That is, the irradiation unit 28 and the radiation source 26 can move independently of each other, and the imaging table 32 and the radiation detector 36 can move independently of each other.

The mammography device 10 includes a thickness detection unit 64 (refer to FIG. 5) that detects the thickness of the breast M in the irradiation direction in a state in which the breast M of the subject P is compressed by the compression plate 40. The thickness detection unit 64 detects the thickness of the breast M in the irradiation direction based on the distance between the surface of the compression plate 40 in contact with the breast M and the imaging surface 32A of the imaging table 32.

Figure 5:
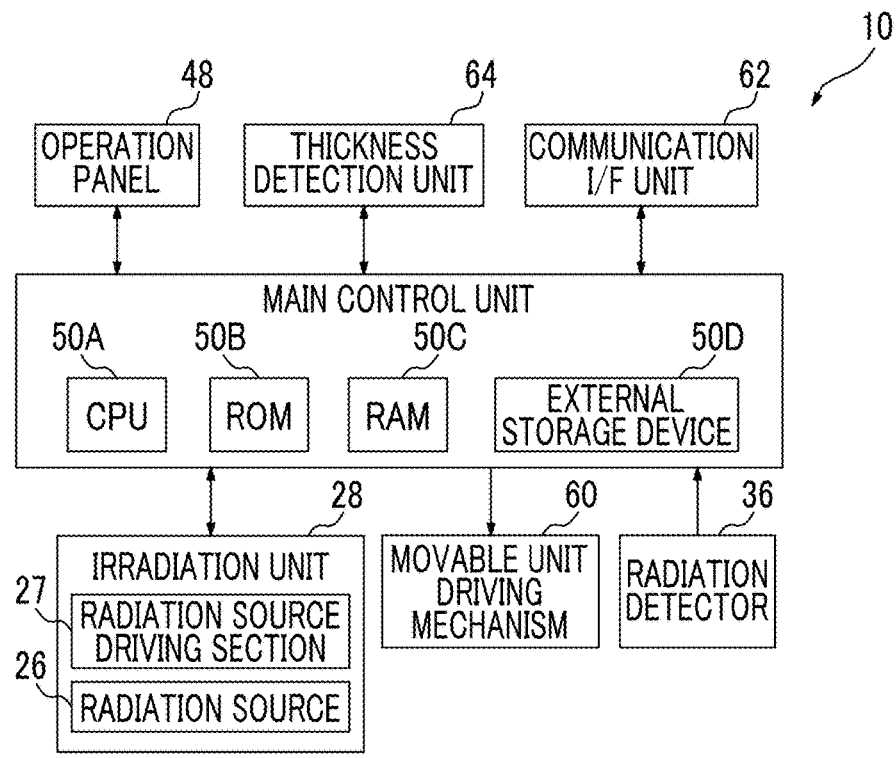
FIG. 5 is a block diagram of the mammography device according to the embodiment of the present invention.

The mammography device 10 includes an operation panel 48 to which various operation instructions are input (refer to FIG. 5). The operation panel 48 may be provided as a part of the mammography device 10, or may be provided in a separate console from the mammography device 10 so as to be able to communicate with the mammography device 10.

Next, the operation of the movable arm unit 16 of the mammography device 10 will be described. The mammography device 10 according to the present embodiment includes the movable arm unit 16 in which the irradiation unit 28 and the radiation source 26 can move independently of each other and the imaging table 32 and the radiation detector 36 can move independently of each other as described above. Therefore, imaging in various imaging modes including CC imaging (craniocaudal imaging), MLO imaging (imaging in an inside-and-outside oblique position), and tomosynthesis imaging is possible.

Figure 4:
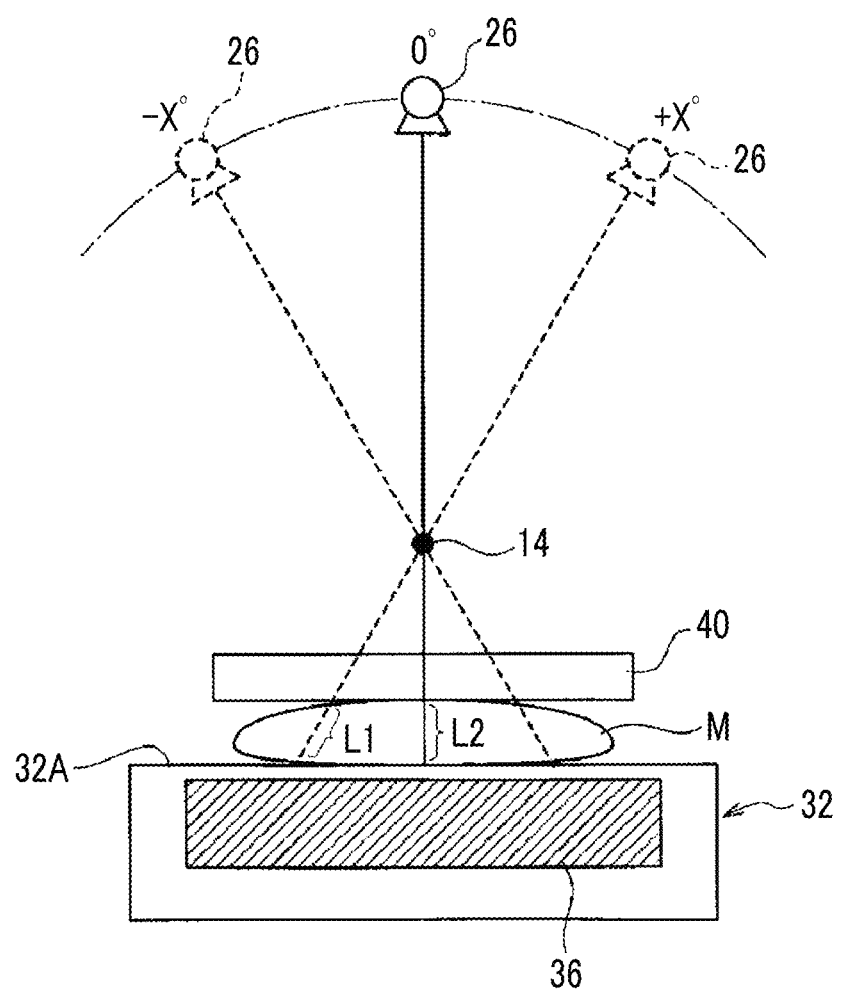
FIG. 4 is a schematic diagram for explaining a tomosynthesis imaging function in the mammography device according to the embodiment of the present invention.

Next, the tomosynthesis imaging function of the mammography device 10 will be described. FIG. 4 is a schematic diagram for explaining the tomosynthesis imaging function of the mammography device 10. According to the tomosynthesis imaging, it is possible to reconstruct a tomographic image using a plurality of projection images acquired by emitting radiation to the breast M from a plurality of directions.

At the time of tomosynthesis imaging in the standing state of the subject P, radiation from the radiation source 26 is emitted at a plurality of emission angles by rotating the movable arm unit 16 around the rotating shaft 14 while fixing the imaging surface 32A of the imaging table 32 so as to face upward.

By the rotation of the movable arm unit 16 around the rotating shaft 14, the radiation source 26 is moved so as to draw an arc above the radiation detector 36, as shown in FIG. 4. For example, in the case of rotation in the positive direction, the radiation source 26 rotates clockwise at predetermined intervals from an angle −X° to an angle +X°. In addition, a direction perpendicular to the imaging surface 32A (detection surface of the radiation detector 36) of the imaging table 32 is defined as an emission angle 0°.

In the tomosynthesis imaging, while compressing the breast M, the angle position of the radiation source 26 with respect to the radiation detector 36 is moved by rotating the movable arm unit 16, and projection images are acquired by emitting radiation to the breast M from a plurality of different directions. By reconstructing the projection images acquired as described above, a tomographic image is generated.

FIG. 5 is a block diagram showing the control configuration of the mammography device 10. As described above, the mammography device 10 includes the irradiation unit 28 including the radiation source 26 and the radiation source driving section 27, the radiation detector 36, the operation panel 48, and the thickness detection unit 64. The mammography device 10 includes the main control unit 50 that performs overall control of the operation of the entire device, a movable unit driving mechanism 60 that drives movable units, such as the rotating shaft 14, the movable arm unit 16, and the compression plate 40, at the time of imaging, and a communication interface unit 62 that transmits and receives various kinds of information to and from other devices connected to a network, such as a local area network (LAN), by being connected to the network.

The main control unit 50 includes a central processing unit (CPU) 50A, a read only memory (ROM) 50B, a random access memory (RAM) 50C, and a nonvolatile external storage device 50D such as a hard disk drive (HDD). The main control unit 50 is connected to each of the irradiation unit 28, the radiation detector 36, the operation panel 48, the thickness detection unit 64, the movable unit driving mechanism 60, and the communication interface unit 62. Various programs executed by the CPU 50A, various kinds of data, and the like are stored in the ROM 50B.

The radiation source driving section 27 and the movable unit driving mechanism 60 are controlled by the main control unit 50. The thickness data indicating the thickness of the breast M generated by the thickness detection unit 64 and the image data indicating the radiographic image generated by the radiation detector 36 are supplied to the main control unit 50. The operation panel 48 notifies the main control unit 50 of information indicating the imaging mode selected in response to the input operation of the user.

Figure 6:
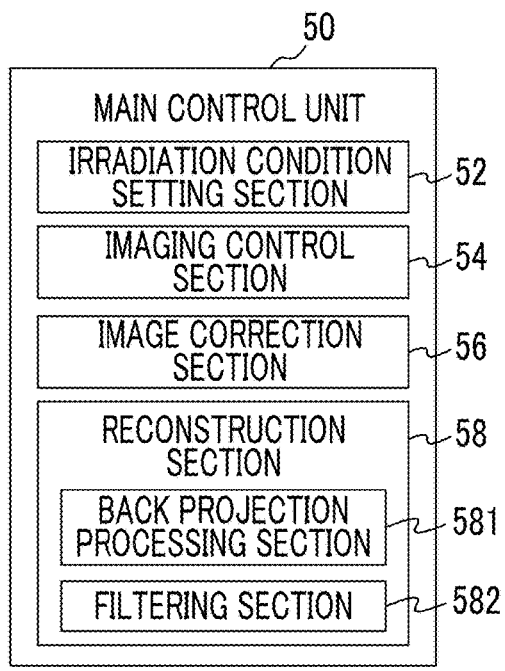
FIG. 6 is a functional block diagram of a main control unit according to the embodiment of the present invention.

FIG. 6 is a functional block diagram showing the functional configuration of the main control unit 50. The main control unit 50 functions as an irradiation condition setting section 52, an imaging control section 54, an image correction section 56, and a reconstruction section 58 when the CUP 50 executes various programs stored in the ROM 50B.

<Setting of Irradiation Conditions>

The irradiation condition setting section 52 is a functional section that sets the irradiation conditions of radiation emitted from the radiation source 26. As described above, in the tomosynthesis imaging, a transmission distance by which the radiation is transmitted through the subject changes according to the emission angle of radiation. That is, as shown in FIG. 4, a transmission distance L1 in the case of emitting the radiation from obliquely above the breast M is longer than a transmission distance L2 in the case of emitting the radiation from directly above the breast M. As the transmission distance increases, attenuation of the radiation in the subject increases. Accordingly, in a case in which the irradiation conditions are fixed, as the transmission distance increases, the dose of radiation that is transmitted through the breast M and reaches the radiation detector 36 decreases, and the SN of the image is reduced.

The dose $I_d$ that reaches the radiation detector 36 can be expressed by the following Equation (1). In Equation (1), $I_0$ is the dose of radiation emitted from the radiation source 26, $\mu$ is the absorption coefficient of radiation transmitted through the subject, and L is the transmission distance of radiation transmitted through the subject.

$$I_d = I_0 \exp(-\mu \cdot L) \tag{1}$$

The transmission distance L is determined according to the thickness of the breast M and the emission angle of radiation. On the other hand, the absorption coefficient μ changes according to the tube voltage. The irradiation condition setting section 52 derives a tube voltage, which is to be set for each emission angle, so that the dose $I_d$ of the radiation that reaches the radiation detector 36 at each emission angle is approximately fixed. More specifically, the irradiation condition setting section 52 emits a relatively low dose of radiation to the breast M (pre-irradiation) before capturing a radiographic image for diagnosis, and derives the absorption coefficient μ from the ratio of the dose of radiation emitted from the radiation source 26 and the dose reaching the radiation detector 36 and the measured thickness of the breast M. The irradiation condition setting section 52 may derive the ratio of mammary glands and fat in a breast region by analyzing an image obtained by pre-irradiation, and derive the absorption coefficient μ based on the derived ratio. Pre-irradiation is performed at the emission angle of 0°, for example. Then, in a case in which the transmission distance L changes with a change in the emission angle of radiation, the irradiation condition setting section 52 derives the absorption coefficient μ for each emission angle based on Equation (1) so that the dose $I_d$ reaching the radiation detector 36 is fixed. That is, the irradiation condition setting section 52 derives the absorption coefficient μ for each emission angle so that L×μ is fixed.

Figure 7A:
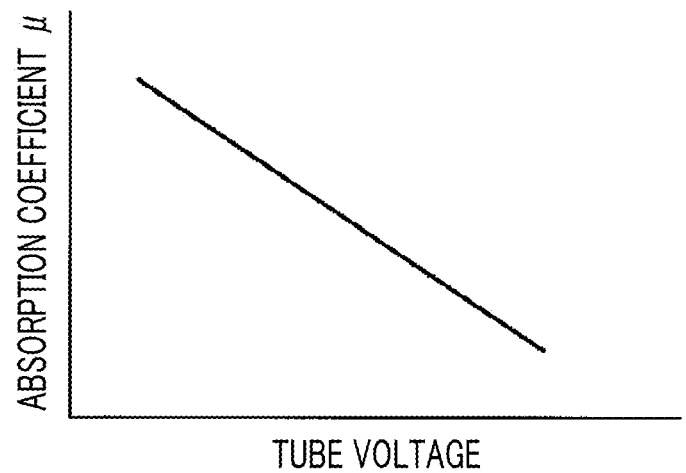
FIG. 7A is a diagram showing the relationship between a tube voltage and an absorption coefficient $\mu$ according to the embodiment of the present invention.

Here, FIG. 7A is a diagram showing an example of the relationship between the tube voltage and the absorption coefficient μ. As shown in FIG. 7A, as the tube voltage increases, the absorption coefficient μ tends to decrease since the radiation is easily transmitted through the subject. Mapping data indicating the relationship between the tube voltage and the absorption coefficient μ as shown in FIG. 7A is stored in the ROM 50B of the main control unit 50. The irradiation condition setting section 52 derives a tube voltage corresponding to the absorption coefficient μ, which has been derived for each emission angle, based on the mapping data stored in the ROM 50B.

Figure 7B:
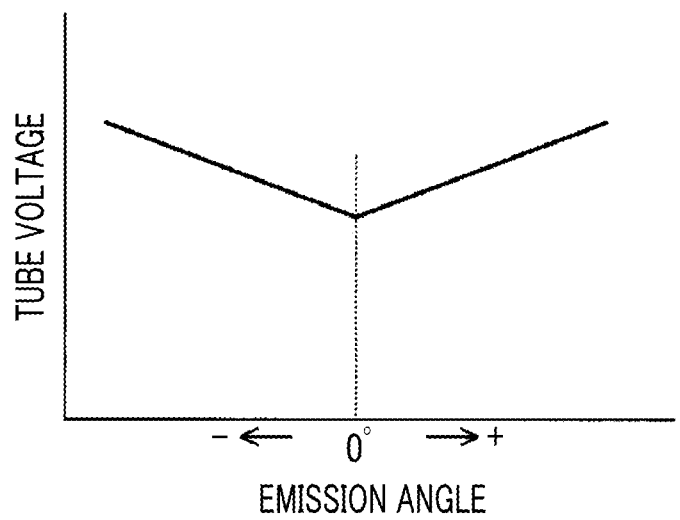
FIG. 7B is a diagram showing the relationship between the emission angle of radiation and the tube voltage according to the embodiment of the present invention.

The irradiation condition setting section 52 sets the irradiation conditions, for example, such that the tube voltage in a case in which the emission angle of radiation is 0° (that is, in a case in which the transmission distance of radiation is the shortest) is the lowest and the tube voltage increases as the emission angle increases to the positive and negative sides (that is, as the transmission distance of radiation increases) as shown in FIG. 7B. Even if the transmission distance L is changed according to the emission angle by setting the tube voltage according to the emission angle of radiation as described above, the dose $I_d$ of radiation reaching the radiation detector 36 is approximately fixed. Therefore, it is possible to make uniform the SN of a plurality of projection images corresponding to the respective emission angles.

In the present embodiment, the irradiation condition setting section 52 sets the irradiation conditions such that the dose $I_0$ of radiation emitted from the radiation source 26 is fixed at each emission angle. That is, for example, tube current and irradiation time are assumed to be approximately fixed at each emission angle.

Figure 8:
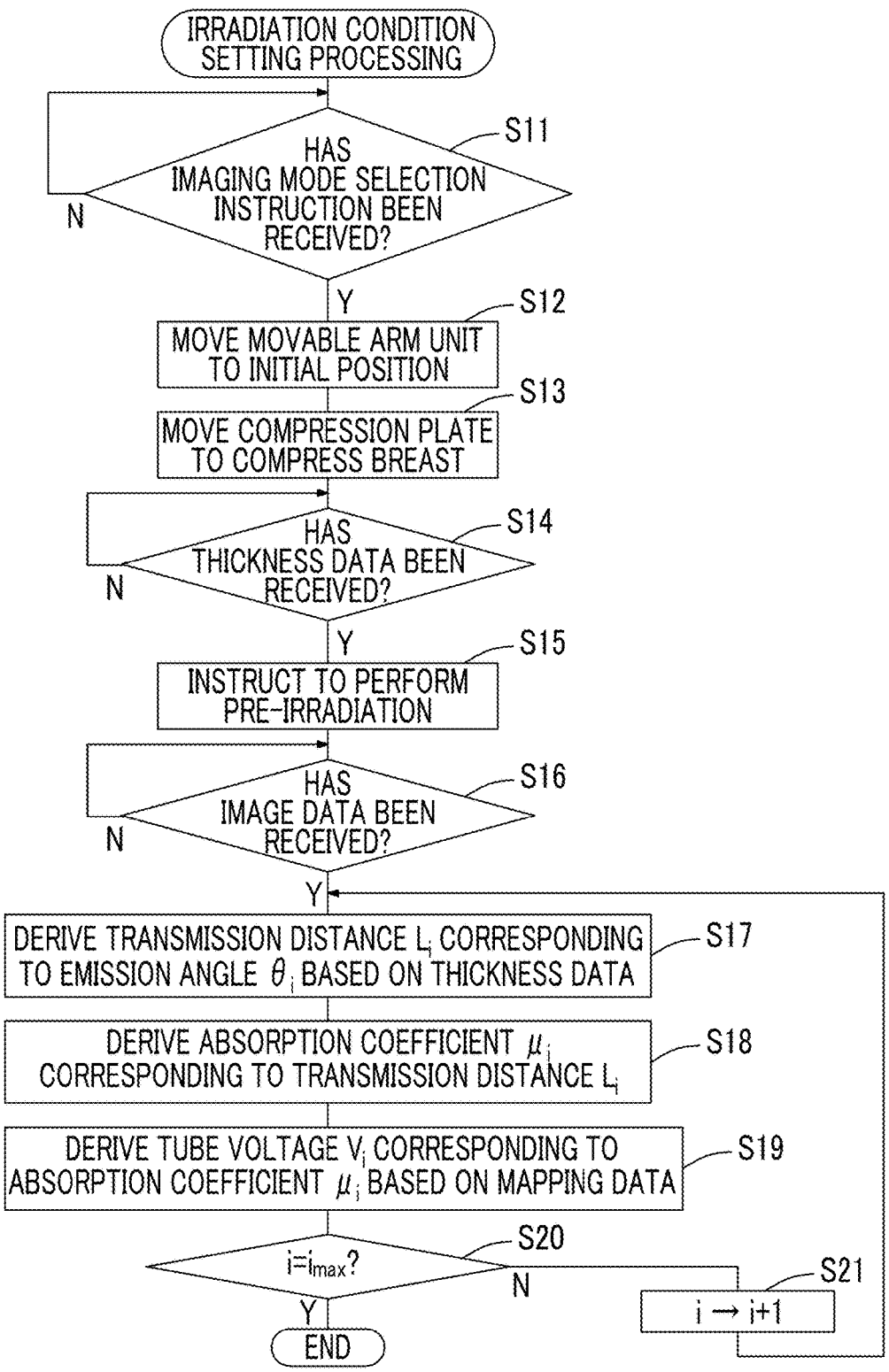
FIG. 8 is a flowchart showing the flow of processing in an irradiation condition setting program according to the embodiment of the present invention.

FIG. 8 is a flowchart showing the flow of the process in an irradiation condition setting program executed by the CPU 50A of the main control unit 50 that functions as the irradiation condition setting section 52. The irradiation condition setting program is stored in the ROM 50B.

In step S11, the CPU 50A waits for the reception of an imaging mode selection instruction. For example, when the user selects one imaging mode of two-dimensional (2D) imaging for performing imaging by emitting radiation from only one direction and tomosynthesis imaging for performing imaging by emitting radiation from a plurality of directions in the operation panel 48, positive determination is made in step S11, and the process proceeds to step S12. Here, it is assumed that the tomosynthesis imaging is selected by the user.

In step S12, the CPU 50A transmits to the movable unit driving mechanism 60 an instruction to set the rotation angle position of the movable arm unit 16 to the initial position. The movable unit driving mechanism 60 that has received the instruction moves the rotation angle position of the movable arm unit 16, for example, so that the emission angle of radiation becomes 0°.

Then, when the positioning of the breast M with respect to the imaging table 32 is performed and an input operation indicating that the positioning of the breast M has been completed is performed on the operation panel 48, the process proceeds to step S13.

In step S13, the CPU 50A transmits to the movable unit driving mechanism 60 an instruction to compress the breast M by moving the compression plate 40 in the direction of the imaging table 32. The movable unit driving mechanism 60 that has received the instruction moves the compression plate 40 to the imaging table 32 so as to be in contact with the breast M. Then, when the pressing force of the compression plate 40 reaches a set value, the movable unit driving mechanism 60 stops the movement of the compression plate 40. When the movement of the compression plate 40 is stopped, the thickness detection unit 64 detects the thickness of the breast M in a direction perpendicular to the imaging surface 32A based on the distance between the surface of the compression plate 40 in contact with the breast M and the imaging surface 32A of the imaging table 32, and transmits thickness data indicating the detected thickness of the breast M to the CPU 50A.

In step S14, the CPU 50A waits for the reception of the thickness data from the thickness detection unit 64. When the CPU 50A receives the thickness data from the thickness detection unit 64, the received thickness data is stored in the RAM 50C, and the process proceeds to step S15.

In step S15, the CPU 50A transmits an instruction to perform pre-irradiation to the radiation source driving section 27. Pre-irradiation refers to the emission of radiation that is performed in order to determine the irradiation conditions in the main irradiation. The main irradiation refers to the emission of radiation that is performed in order to acquire a radiographic image for diagnosis. In addition, the dose of radiation in the pre-irradiation is set to a value smaller than the dose of radiation in the main irradiation. The radiation source driving section 27 that has received the instruction to perform pre-irradiation drives the radiation source 26 to emit radiation under predetermined irradiation conditions. Then, radiation is emitted at the emission angle of 0° from the radiation source 26, so that the pre-irradiation is performed on the breast M. The radiation transmitted through the breast M is emitted to the radiation detector 36. The radiation detector 36 generates a radiographic image corresponding to the dose distribution of radiation transmitted through the breast M, and transmits image data indicating the radiographic image to the CPU 50A.

In step S16, the CPU 50A waits for the reception of the image data based on the pre-irradiation from the radiation detector 36. When the image data is received from the radiation detector 36, the process proceeds to step S17.

In step S17, the CPU 50A derives the transmission distance $L_i$ corresponding to the emission angle $θ_i$ of radiation based on the thickness data indicating the thickness of the breast M acquired in step S14.

In step S18, the CPU 50A derives the absorption coefficient μ corresponding to the emission angle of 0° based on the radiographic image based on the pre-irradiation that has been received in step S16. Then, based on Equation (1) described above, the CPU 50A derives the absorption coefficient $\mu_i$ corresponding to the transmission distance $L_i$ derived in step S17 so that the dose $I_d$ of radiation reaching the radiation detector 36 during the main irradiation becomes a predetermined value. In the present embodiment, the dose $I_0$ of radiation emitted from the radiation source 26 is approximately fixed at each emission angle.

In step S19, the CPU 50A derives a tube voltage $V_i$ corresponding to the absorption coefficient $\mu_i$ derived in step S18 based on the mapping data (refer to FIG. 7A) indicating the relationship between the tube voltage and the absorption coefficient that is stored in the ROM 50B.

In step S20, the CPU 50A determines whether or not the value of i is a predetermined value $i_{max}$. That is, in this step, it is determined whether or not the derivation of the tube voltage at all emission angles has ended. The CPU 50A proceeds to step S21 in a case in which it is determined that the value of i is not $i_{max}$, and ends this routine in a case in which it is determined that the value of i is $i_{max}$.

In step S21, the CPU 50A increments the value of i by 1, and returns the process to step S17. By repeatedly performing the processing from step S17 to step S21, a tube voltage corresponding to each emission angle is derived.

In the present embodiment, the transmission distance L is derived based on the measurement value of the thickness of the breast M. However, the transmission distance L may be derived on the assumption that the thickness of the breast M is fixed. That is, it is possible to omit the measurement of the thickness of the breast M in this case. In addition, the mapping data (refer to FIG. 7A) indicating the relationship between the tube voltage and the absorption coefficient may be modified based on the image data based on the pre-irradiation that has been received in step S16. For example, the CPU 50A may modify the mapping data to shift the curve of the absorption coefficient μ shown in FIG. 7A upward in a case in which it is determined that the breast density of the breast M is higher than the standard from the image data based on the pre-irradiation and to shift the curve of the absorption coefficient downward in a case in which it is determined that the breast density is lower than the standard. In addition, the irradiation condition setting section 52 may set the tube voltage at each emission angle of radiation to a value, which is set in advance according to each emission angle, regardless of the composition or the thickness of the breast M. In the present embodiment, the pre-irradiation is performed at the emission angle of 0°. However, the pre-irradiation may be performed at the maximum emission angle (−X° or +X° shown in FIG. 4).

In the present embodiment, the tube voltage is adjusted according to the emission angle so that the dose of radiation reaching the radiation detector 36 is fixed. However, in addition to this, the tube current and the irradiation time (that is, the dose $I_0$ of radiation emitted from the radiation source 26) may be adjusted. By setting the dose $I_0$ in the case of emitting radiation from obliquely above the breast M to be larger than the dose $I_0$ in the case of emitting radiation from directly above the breast M, the dose $I_d$ of radiation reaching the radiation detector 36 can be made uniform as in the case of adjusting the tube voltage. In this case, however, since the amount of exposure to the breast M is increased, it is preferable to adjust the dose $I_d$ by changing the tube voltage in a state in which the dose $I_0$ of radiation emitted from the radiation source 26 is fixed.

<Capturing of a Radiographic Image>

The imaging control section 54 is a functional section that controls the irradiation unit 28, the radiation detector 36, and the movable unit driving mechanism 60 in order to acquire a radiographic image by emitting radiation based on the irradiation conditions set by the irradiation condition setting section 52.

Figure 9:
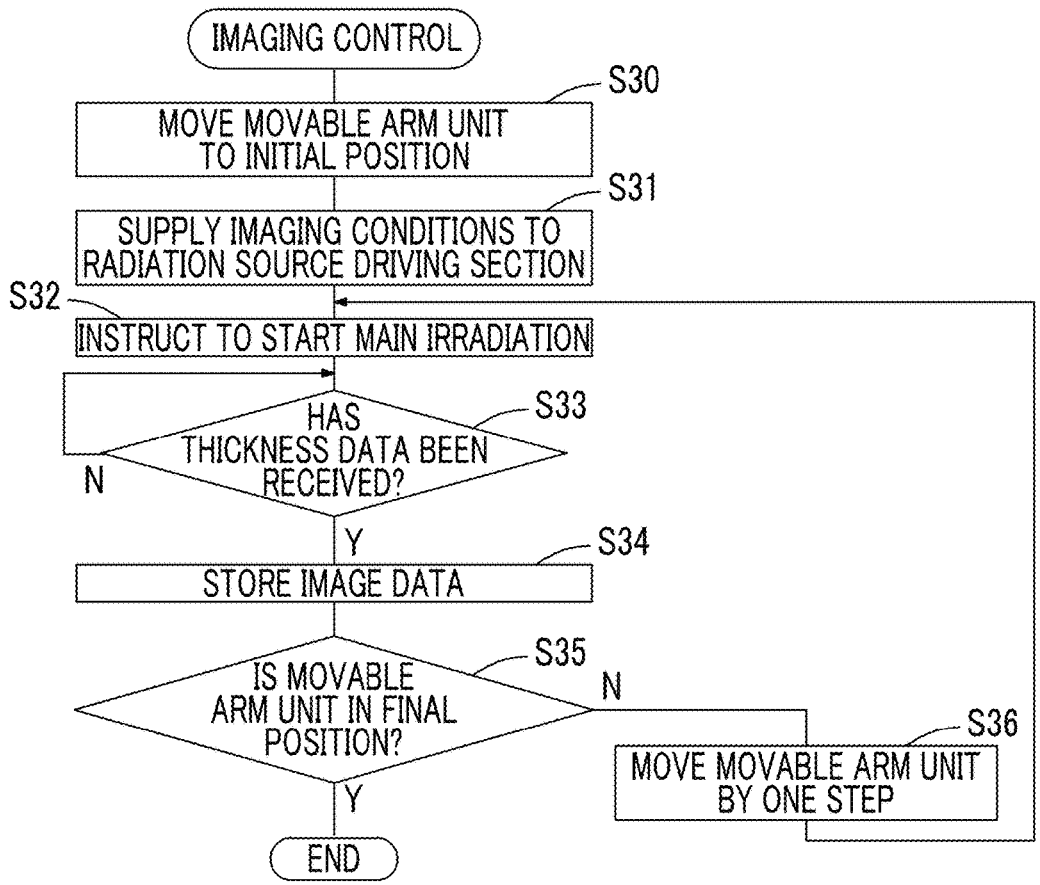
FIG. 9 is a flowchart showing the flow of processing in an imaging control program according to the embodiment of the present invention.

FIG. 9 is a flowchart showing the flow of the process in an imaging control program executed by the CPU 50A that functions as the imaging control section 54. The imaging control program is stored in the ROM 50B, and is executed when the irradiation condition setting program (refer to FIG. 8) is ended. That is, the processing in the irradiation condition setting program and the processing in the imaging control program are executed as a series of processes.

In step S30, the CPU 50A transmits to the movable unit driving mechanism 60 an instruction to set the rotation angle position of the movable arm unit 16 to the initial position in tomosynthesis imaging. The movable unit driving mechanism 60 that has received the instruction moves the movable arm unit 16 to the rotation angle position (position of −X° shown in FIG. 4) having the largest inclination, for example.

In step S31, the CPU 50A supplies information indicating the irradiation conditions, which include the tube voltage, the tube current, and the irradiation time at each emission angle of radiation that have been derived by executing the irradiation condition setting program described above, to the radiation source driving section 27.

In step S32, the CUP 50A instructs the radiation source driving section 27 to start irradiation (main irradiation). The radiation source driving section 27 that has received the instruction drives the radiation source 26 to emit radiation under the irradiation conditions corresponding to the current rotation angle position (that is, the current emission angle of radiation) of the movable arm unit 16. That is, as shown in FIG. 7B, the radiation source driving section 27 drives the radiation source 26 so that the tube voltage is changed according to the emission angle of radiation. Accordingly, radiation is emitted from the radiation source 26, so that the main irradiation is performed on the breast M. The radiation transmitted through the breast M is emitted to the radiation detector 36. The radiation detector 36 generates a radiographic image corresponding to the dose distribution of radiation transmitted through the breast M, and transmits image data indicating the radiographic image to the CPU 50A.

In step S33, the CPU 50A waits for the reception of the image data based on the main irradiation from the radiation detector 36. When the image data is received from the radiation detector 36, the process proceeds to step S34. In step S34, the CPU 50A stores the acquired image data in the external storage device 50D.

In step S35, the CPU 50A determines whether or not the rotation angle position of the movable arm unit 16 is in a final position (in the present embodiment, a position of +X°), and the process proceeds to step S36 in a case in which the rotation angle position of the movable arm unit 16 is not in the final position.

In step S36, the CPU 50A transmits to the movable unit driving mechanism 60 an instruction to move the rotation angle position of the movable arm unit 16 by one step in the positive direction. The movable unit driving mechanism 60 that has received the instruction moves the rotation angle position of the movable arm unit 16 by one step in the positive direction. When the movement of the movable arm unit 16 is completed, the CPU 50A repeatedly performs the processing from step S32 to step S35. Accordingly, irradiation is performed multiple times while the movable arm unit 16 moves from −X° to +X°, and image data is acquired for each angle position of the movable arm unit 16. Each piece of the acquired image data is stored in the external storage device 50D.

When the CPU 50A determines that the rotation angle position of the movable arm unit 16 is in a final position in step S35, this routine is ended.

By executing the imaging control program, radiation is emitted to the breast M from the radiation source 26 at a plurality of different emission angles in the tomosynthesis imaging. Accordingly, a projection image is generated for each emission angle. According to the mammography device 10 of the present embodiment, the irradiation conditions are set such that the tube voltage increases as the transmission distance increases according to the emission angle of radiation. Therefore, the SN becomes uniform in a plurality of projection images corresponding to the respective emission angles.

<Correction of Density and Contrast of a Radiographic Image>

Figure 10A:
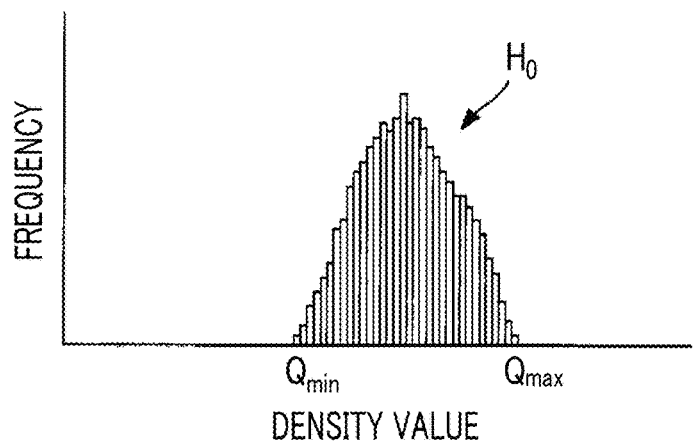
FIG. 10A is a diagram showing an example of the density histogram of a projection image captured by setting the emission angle of radiation to 0°.
Figure 10B:
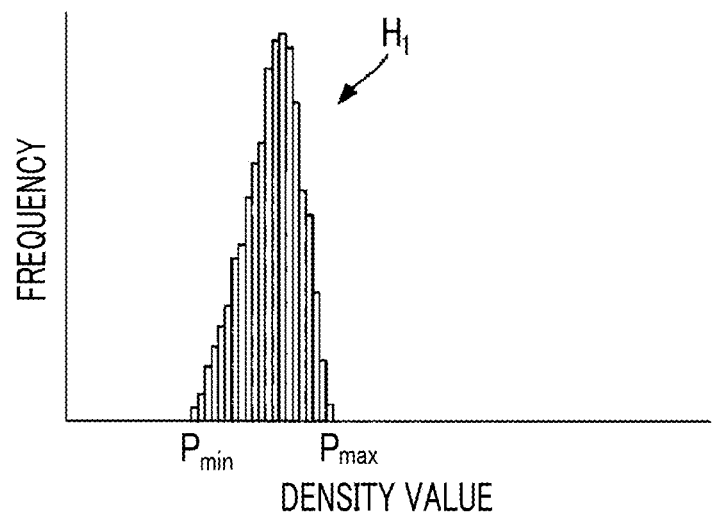
FIG. 10B is a diagram showing an example of a density histogram $H_i$ of a projection image captured by setting the emission angle of radiation to $\theta_i$ ($\theta_i \neq 0°$).

FIG. 10A is a diagram showing an example of a density histogram $H_0$ of a projection image captured by setting the emission angle of radiation to 0°. FIG. 10B is a diagram showing an example of a density histogram $H_i$ of a projection image captured by setting the emission angle of radiation to $\theta_i$ ($\theta_i \neq 0°$). The density histogram is a frequency distribution in which a density value (pixel value) in each pixel of the projection image generated by the radiation detector 36 is on the horizontal axis and the density value is on the vertical axis. In the mammography device 10 according to the present embodiment, when the emission angle of radiation is 0°, the tube voltage is the smallest. Accordingly, since the X-ray absorption difference is likely to be reflected in the image, a high-contrast projection image is obtained. Therefore, the density histogram $H_0$ corresponding to the emission angle of 0° shows a wider shape than the density histogram $H_i$ corresponding to the emission angle $\theta_i$ ($\theta_i \neq 0°$).

On the other hand, in the case of the emission angle $\theta_i$ ($\theta_i \neq 0°$), a higher tube voltage than in the case of the emission angle of 0° is set. Accordingly, the density histogram $H_i$ is located on the lower density side on the whole than in the density histogram $H_0$. Thus, according to the mammography device 10 of the present embodiment, projection images are captured by setting different tube voltages for the respective emission angles of radiation. Therefore, the SN of the projection image at each emission angle is uniform, and the density values and the contrasts of projection images are not uniform. In general, the contrast C of an image is expressed by the following Equation (2). In Equation (2), $P_{max}$ is a maximum density value of the image, and $P_{min}$ is the minimum density value of the image.

$$C = (P_{max} - P_{min})/(P_{max} + P_{min}) \quad (2)$$

Reconstructing a tomographic image using a plurality of projection images having density values and contrasts that are not uniform may cause a reduction in the quality of the tomographic image.

The image correction section 56 is a functional section that corrects each projection image so that the differences between the density values and the contrasts of projection images at the respective emission angles acquired by tomosynthesis imaging are reduced. The image correction section 56 corrects the density value and the contrast in each projection image so that the density value and the contrast of the projection image at each emission angle are approximately uniform, before reconstructing the tomographic image based on the projection image at each emission angle.

Figure 10C:
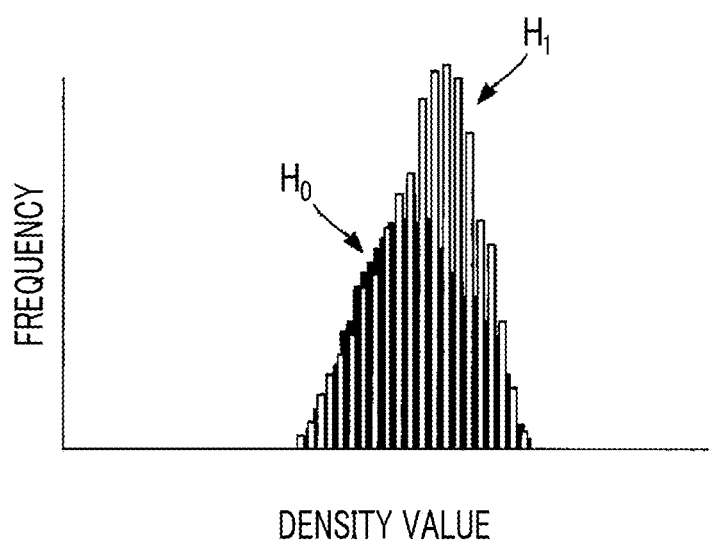
FIG. 10C is a diagram showing an example of a density histogram after the correction of a projection image corresponding to the emission angle $\theta_i$ ($\theta_i \neq 0°$).

Hereinafter, the image correction of the image correction section 56 will be described. The image correction section 56 generates the density histograms shown in FIGS. 10A and 10B for each projection image at each emission angle acquired by tomosynthesis imaging. For example, the image correction section 56 sets the density histogram $H_0$, which is generated for a projection image corresponding to the emission angle of 0° at which the set value of the tube voltage is the smallest, as a reference histogram, and corrects a projection image corresponding to the emission angle $\theta_i$ ($\theta_i \neq 0°$) so that the difference between the reference histogram (density histogram $H_0$) and the density histogram $H_i$ generated for a projection image corresponding to the emission angle $\theta_i$ ($\theta_i \neq 0°$) is reduced. FIG. 10C is a diagram showing an example of a density histogram after the correction of a projection image corresponding to the emission angle $\theta_i$ ($\theta_i \neq 0°$).

For example, the image correction section 56 converts the density value of each pixel of the projection image corresponding to the emission angle $\theta_i$ ($\theta_i \neq 0°$) so that the area of the overlapping portion between the density histogram $H_0$ (reference histogram) corresponding to the emission angle of 0° and the density histogram $H_i$ corresponding to the emission angle $\theta_i$ ($\theta_i \neq 0°$) is maximized. The image correction section 56 derives a density value Q of each pixel after the correction based on the following Equation (3), for example. In Equation (3), P is the density value of an arbitrary pixel before correction, a and b are correction coefficients, a is a gain, and b is an offset.

$$Q = aP + b \quad (3)$$

That is, according to Equation (3), the density value of each pixel is linearly converted. According to the linear conversion, it is possible to adjust the range of the density distribution, that is, the contrast using the gain a, and it is possible to adjust the average density value, that is, the brightness of the entire image using the offset b. The image correction section 56 derives the gain a and the offset b at which the area of the overlapping portion between the density histogram $H_0$ (reference histogram) corresponding to the emission angle of 0° and the density histogram $H_i$ corresponding to the emission angle $\theta_i$ ($\theta_i \neq 0°$) is maximized. The image correction section 56 converts the density value of each pixel of the projection image corresponding to the emission angle $\theta_i$ ($\theta_i \neq 0°$) based on the conversion function expressed by Equation (3). Therefore, the density value and the contrast of the projection image corresponding to the emission angle $\theta_i$ ($\theta_i \neq 0°$) can be brought close to the density value and the contrast of the projection image corresponding to the emission angle of 0° (refer to FIG. 10C).

A high-quality tomographic image can be obtained by reconstructing a tomographic image using a plurality of projection images between which a density value difference and a contrast difference have been reduced. The projection image corresponding to the emission angle of 0° has higher contrast than the projection image corresponding to the emission angle $\theta_i$ ($\theta_i \neq 0°$). Therefore, by setting the density histogram $H_0$ corresponding to the emission angle of 0° as a reference histogram, it is possible to maintain the high contrast in the reconstructed tomographic image. In FIG. 10C, a case is shown in which the maximum and minimum values of the density in the density histogram $H_0$ match the maximum and minimum values of the density in the density histogram $H_i$. However, a and b may be calculated so that the area of the overlapping portion between the density histogram $H_0$ and the density histogram $H_i$ is maximized, and the maximum and minimum values of the density in the density histogram $H_0$ do not necessarily match the maximum and minimum values of the density in the density histogram $H_i$. In addition, an area calculation section that calculates the area of the overlapping portion between the density histogram $H_0$ and the density histogram $H_i$ may be included in the image correction section 56.

Figure 11:
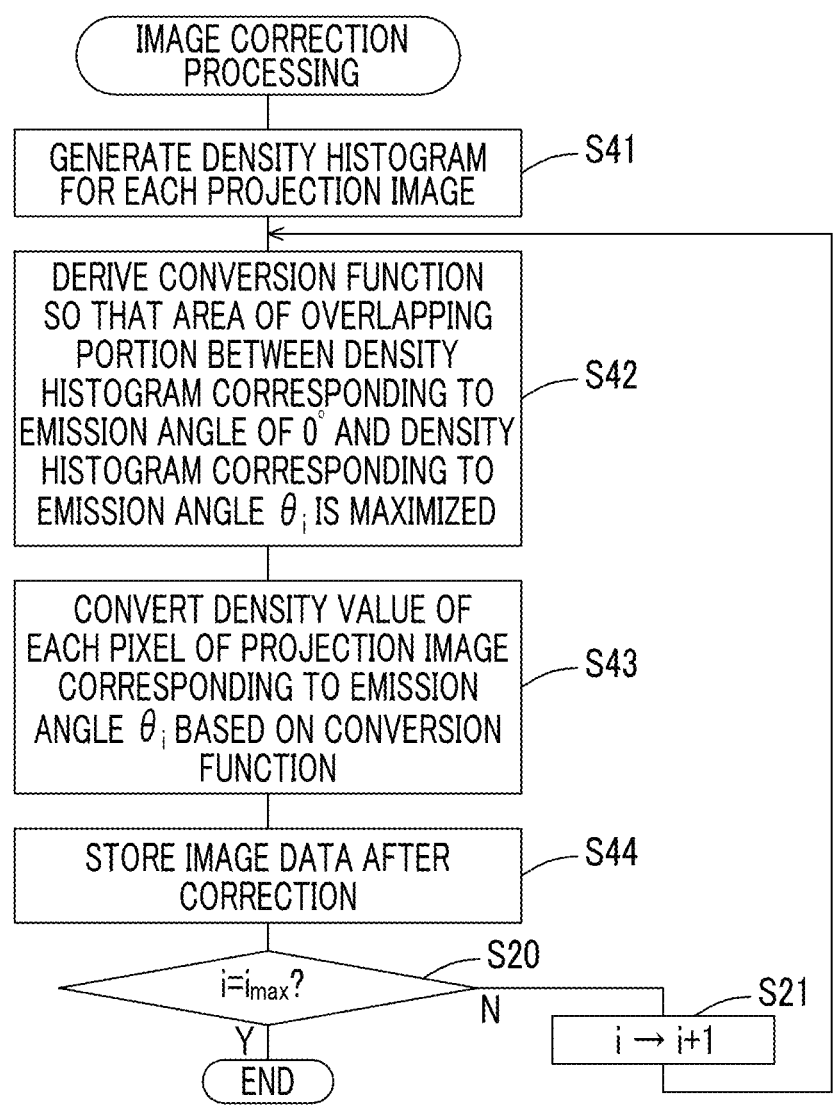
FIG. 11 is a flowchart showing the flow of processing in an image correction program according to another embodiment of the present invention.

FIG. 11 is a flowchart showing the flow of the process in an image correction program executed by the CPU 50A that functions as the image correction section 56. The image correction program is stored in the ROM 50B.

In step S41, the CPU 50A generates a density histogram for each projection image at each emission angle acquired by executing the imaging control program described above (refer to FIG. 9).

In step S42, the CPU 50A derives a conversion function for converting the density value of each pixel of the projection image corresponding to the emission angle $\theta_i$ ($\theta_i \neq 0°$). Specifically, the CPU 50A derives the gain a and the offset b of the conversion function expressed by Equation (3) so that the area of the overlapping portion between the density histogram $H_0$ (reference histogram) corresponding to the emission angle of 0° and the density histogram $H_i$ corresponding to the emission angle $\theta_i$ ($\theta_i \neq 0°$) is maximized.

In step S43, the CPU 50A corrects the density value and the contrast of the projection image by converting the density value in each pixel of the projection image corresponding to the emission angle $\theta_i$ ($\theta_i \neq 0°$) based on the conversion function derived in step S42.

In step S44, the CPU 50A stores image data of the projection image after the correction in the external storage device 50D.

In step S45, the CPU 50A determines whether or not the value of i is a predetermined value $i_{max}$. That is, in this step, it is determined whether or not the correction of all projection images has been completed. The CPU 50A proceeds to step S46 in a case in which it is determined that the value of i is not $i_{max}$, and ends this routine in a case in which it is determined that the value of i is $i_{max}$.

In step S46, the CPU 50A increments the value of i by 1, and returns the process to step S42. Correction processing on each projection image corresponding to each emission angle is performed by repeatedly performing the processing from step S42 to step S44, and image data after the correction is stored in the external storage device 50D.

<Reconstruction of a Tomographic Image>

The reconstruction section 58 is a functional section that reconstructs a tomographic image based on the projection image corresponding to the emission angle of 0° and the projection image corresponding to the emission angle $\theta_i$ ($\theta_i \neq 0°$) that has been corrected by the image correction section 56.

The reconstruction section 58 reconstructs a tomographic image using a known filtered back projection (FBP) method, for example. As shown in FIG. 6, the reconstruction section 58 is configured to include a filtering section 581 and a back projection processing section 582.

In a case in which a projection image is simply backprojected, a blur occurs around the subject. The filtering section 581 performs processing for superimposing a correction function for removing the blur in each projection image on the projection image before performing back projection of the projection image. Specifically, the filtering section 581 converts the image data of each projection image into data in a frequency domain by performing a one-dimensional Fourier transform, modifies the image data by multiplying the data in the frequency domain by a filter function, and performs an inverse Fourier transform to return to data in a spatial domain. The back projection processing section 582 generates a tomographic image by performing back projection of each projection image that has been subjected to filtering processing by the filtering section 581.

In the present embodiment, a tomographic image is reconstructed using a back projection method. However, the present invention is not limited thereto, and other known reconstruction methods (for example, a shift addition method or an iterative reconstruction method described in JP2011-125698A) may also be used.

As is apparent from the above explanation, according to the mammography device 10 of the embodiment of the present invention, the irradiation conditions are set such that the tube voltage increases as the transmission distance of radiation increases. Therefore, even if the transmission distance is changed according to the emission angle of radiation, the SN of a plurality of projection images can be made uniform.

For example, the image correction section 56 derives a conversion function for maximizing the area of the overlapping portion between the density histogram $H_0$ corresponding to the emission angle of 0° and the density histogram $H_i$ corresponding to the emission angle $\theta_i$ ($\theta_i \neq 0°$), and converts the density value of each pixel of the projection image corresponding to the emission angle $\theta_i$ ($\theta_i \neq 0°$) based on the conversion function. Therefore, the density value and the contrast of the projection image corresponding to the emission angle $\theta_i$ ($\theta_i \neq 0°$) can be brought close to the density value and the contrast of the radiographic image corresponding to the emission angle of 0°. Thus, by making the density value and the contrast uniform in a plurality of projection images, it is possible to improve the quality of the reconstructed tomographic image than in the related art.

In addition, since the density histogram $H_0$ corresponding to the emission angle of 0° is set as a reference histogram, it is possible to maintain the high contrast in the reconstructed tomographic image.

In the embodiment described above, the image correction section 56 converts the density value of the projection image corresponding to the emission angle $\theta_i$ ($\theta_i \neq 0°$) so that the area of the overlapping portion between the density histogram $H_0$ corresponding to the emission angle of 0° and the density histogram $H_i$ corresponding to the emission angle $\theta_i$ ($\theta_i \neq 0°$) is maximized. However, the image correction processing performed by the image correction section 56 is not limited to this aspect. Modification examples of the image correction processing performed by the image correction section 56 are shown below.

(Modification Example 1)

The image correction section 56 may linearly convert the density value of each pixel of the projection image corresponding to the emission angle $\theta_i$ ($\theta_i \neq 0°$) so that the minimum density value $P_{min}$ and the maximum density value $P_{max}$ in the projection image corresponding to the emission angle $\theta_i$ ($\theta_i \neq 0°$) match the minimum density value $Q_{min}$ and the maximum density value $Q_{max}$ in the projection image corresponding to the emission angle of 0°.

In this case, the gain a in the conversion function expressed by Equation (3) can be derived based on the following Equation (4), and the offset b can be derived based on the following Equation (5).

$$a = (Q_{max} - Q_{min})/(P_{max} - P_{min}) \quad (4)$$

$$b = Q_{min} - aP_{min} = (Q_{min}P_{max} - Q_{max}P_{min})/(P_{max} - P_{min}) \quad (5)$$

The image correction section 56 converts the density value of each pixel of the projection image corresponding to the emission angle $\theta_i$ ($\theta_i \neq 0°$) based on the conversion function that is derived based on Equations (3) and (4). Even if the density value conversion is performed so that the maximum density values match each other and the minimum density values match each other between projection images as described above, it is possible to reduce the density difference and the contrast difference between the projection images.

Figure 12:
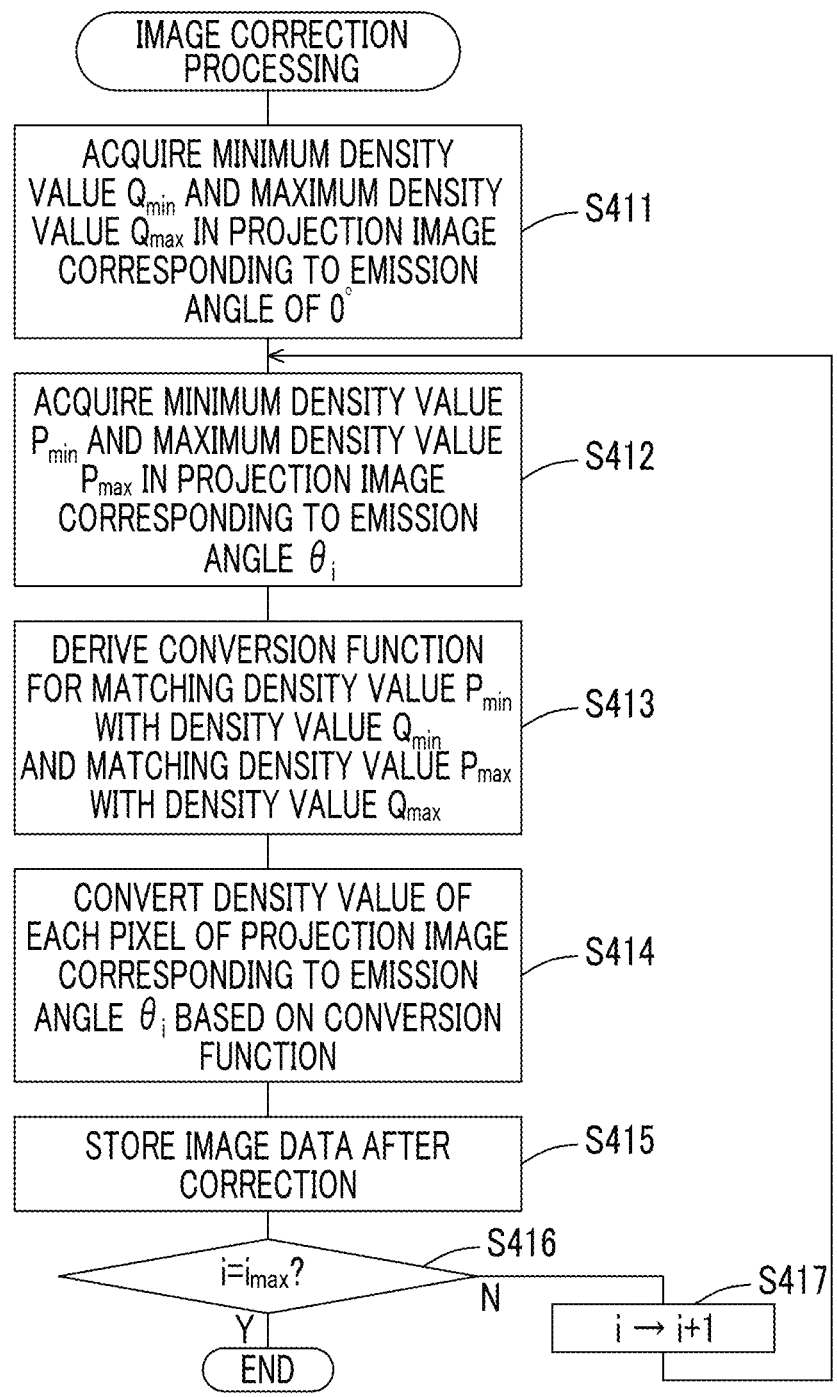
FIG. 12 is a flowchart showing the flow of processing in an image correction program according to another embodiment of the present invention.

FIG. 12 is a flowchart showing the flow of processing in an image correction program according to the modification example 1.

In step S411, the CPU 50A acquires the minimum density value $Q_{min}$ and the maximum density value $Q_{max}$ in the projection image corresponding to the emission angle of 0°.

In step S412, the CPU 50A acquires the minimum density value $P_{min}$ and the maximum density value $P_{max}$ in the projection image corresponding to the emission angle $\theta_i$ ($\theta_i \neq 0°$).

In step S413, the CPU 50A derives a conversion function for matching the density value $P_{min}$ with the density value $Q_{min}$ and matching the density value $P_{max}$ with the density value $Q_{max}$. Specifically, the CPU 50A derives the gain a and the offset b of the conversion function expressed by Equation (3) based on Equations (4) and (5).

In step S414, the CPU 50A corrects the density value and the contrast of the projection image by converting the density value in each pixel of the projection image corresponding to the emission angle $\theta_i$ ($\theta_i \neq 0°$) based on the conversion function derived in step S413.

In step S415, the CPU 50A stores image data of the projection image after the correction in the external storage device 50D.

In step S416, the CPU 50A determines whether or not the value of i is a predetermined value $i_{max}$. That is, in this step, it is determined whether or not the correction of all projection images has been completed. The CPU 50A proceeds to step S417 in a case in which it is determined that the value of i is not $i_{max}$, and ends this routine in a case in which it is determined that the value of i is $i_{max}$.

In step S417, the CPU 50A increments the value of i by 1, and returns the process to step S412. Correction processing on each projection image corresponding to each emission angle is performed by repeatedly performing the processing from step S412 to step S415, and image data after the correction is stored in the external storage device 50D.

After setting the gain a based on Equation (4), the offset b may be derived so that the average density value or the density value of the maximum frequency (hereinafter, referred to as a peak density value) in the projection image corresponding to the emission angle of 0° matches that in the projection image corresponding to the emission angle $\theta_i$ ($\theta_i \neq 0°$).

(Modification Example 2)

The image correction section 56 may linearly convert the density value of each pixel of the projection image corresponding to the emission angle $\theta_i$ ($\theta_i \neq 0°$) so that density values when the cumulative number of pixels in the case of counting pixels in the order of density values reaches, for example, 10% and 90% of the total number of pixels match between the projection image corresponding to the emission angle of 0° and the projection image corresponding to the emission angle $\theta_i$ ($\theta_i \neq 0°$).

Figure 13:
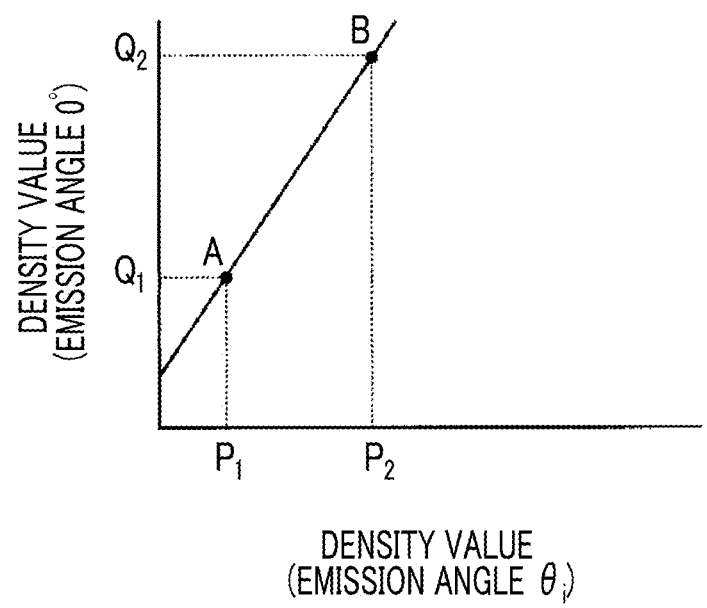
FIG. 13 is a diagram showing the concept of a density value conversion method according to another embodiment of the present invention.

FIG. 13 is a diagram showing the concept of the density value conversion method. In the graph shown in FIG. 13, the horizontal axis indicates the density value of the projection image corresponding to the emission angle $\theta_i$ ($\theta_i \neq 0°$), and the vertical axis indicates the density value of the projection image corresponding to the emission angle of 0°. $P_1$ is a density value when the cumulative number of pixels in the case of counting the pixels of the projection image corresponding to the emission angle $\theta_i$ ($\theta_i \neq 0°$) in the order of density values reaches 10% of the total number of pixels, and $P_2$ is a density value when the cumulative number of pixels in the case of counting the pixels of the projection image corresponding to the emission angle $\theta_i$ ($\theta_i \neq 0°$) in the order of density values reaches 90% of the total number of pixels. $Q_1$ is a density value when the cumulative number of pixels in the case of counting the pixels of the projection image corresponding to the emission angle of 0° in the order of density values reaches 10% of the total number of pixels, and $Q_2$ is a density value when the cumulative number of pixels in the case of counting the pixels of the projection image corresponding to the emission angle of 0° in the order of density values reaches 90% of the total number of pixels. It is possible to plot a point A based on the density values $P_1$ and $Q_1$, and it is possible to plot a point B from the density values $P_2$ and $Q_2$. Then, it is possible to derive the conversion function shown in Equation (3) based on the straight line connecting the points A and B to each other. The image correction section 56 converts the density value of each pixel of the projection image corresponding to the emission angle $\theta_i$ ($\theta_i \neq 0°$) based on the conversion function derived as described above. Even if the density value conversion is performed as described above, it is possible to reduce the density difference and the contrast difference between the images.

Figure 14:
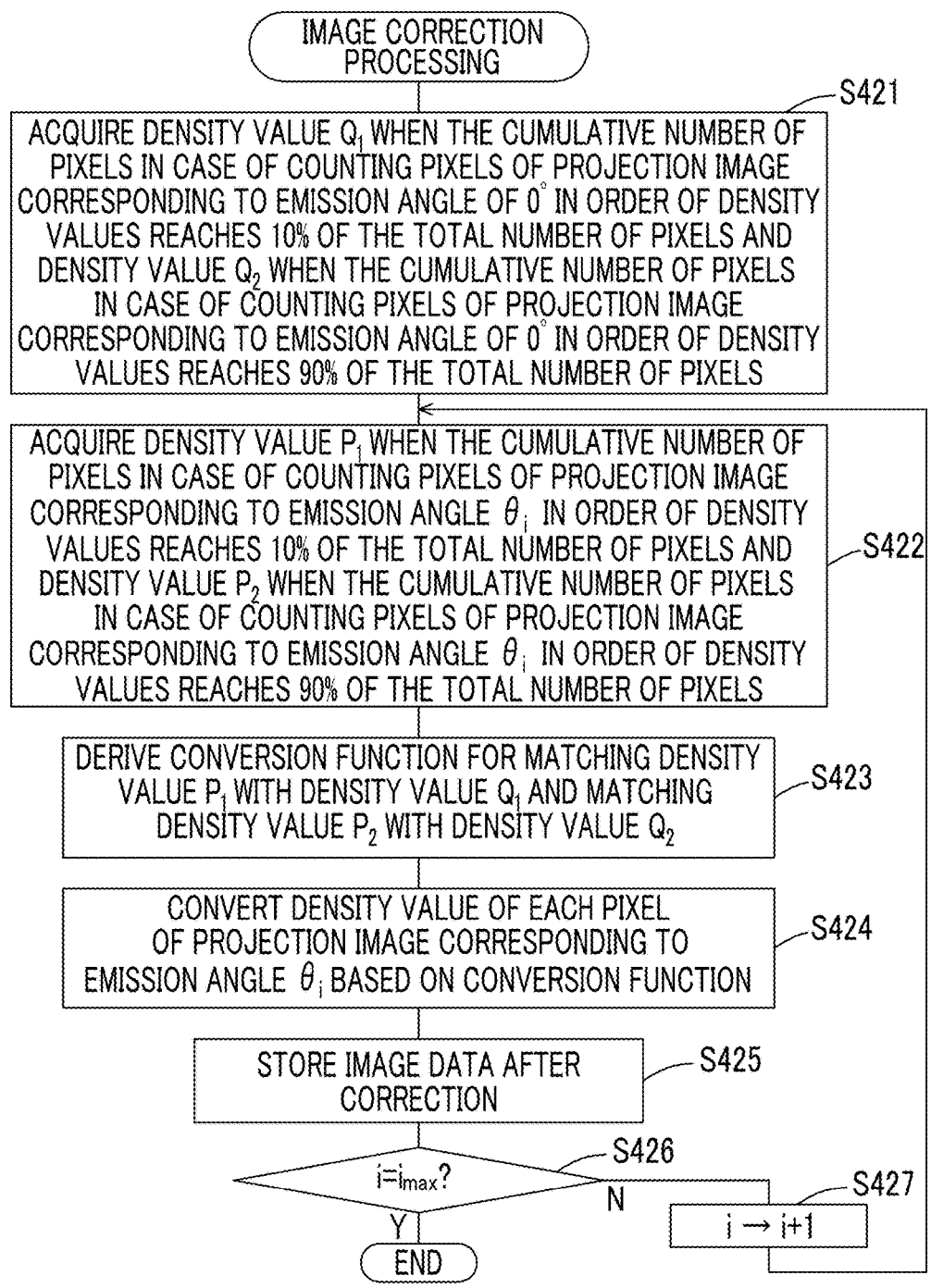
FIG. 14 is a flowchart showing the flow of processing in an image correction program according to another embodiment of the present invention.

FIG. 14 is a flowchart showing the flow of processing in an image correction program according to the modification example 2.

In step S421, the CPU 50A acquires the density value $Q_1$ when the cumulative number of pixels in the case of counting the pixels of the projection image corresponding to the emission angle of 0° in the order of density values reaches 10% of the total number of pixels and the density value $Q_2$ when the cumulative number of pixels in the case of counting the pixels of the projection image corresponding to the emission angle of 0° in the order of density values reaches 90% of the total number of pixels.

In step S422, the CPU 50A acquires the density value $P_1$ when the cumulative number of pixels in the case of counting the pixels of the projection image corresponding to the emission angle $\theta_i$ ($\theta_i \neq 0°$) in the order of density values reaches 10% of the total number of pixels and the density value $P_2$ when the cumulative number of pixels in the case of counting the pixels of the projection image corresponding to the emission angle $\theta_i$ ($\theta_i \neq 0°$) in the order of density values reaches 90% of the total number of pixels.

In step S423, the CPU 50A derives a conversion function for matching the density value $P_1$ with the density value $Q_1$ and matching the density value $P_2$ with the density value $Q_2$. Specifically, the CPU 50A derives the gain a and the offset b of the conversion function expressed by Equation (3) from the straight line connecting the points A and B shown in FIG. 14 to each other.

In step S424, the CPU 50A corrects the density value and the contrast of the projection image by converting the density value in each pixel of the projection image corresponding to the emission angle $\theta_i$ ($\theta_i \neq 0°$) based on the conversion function derived in step S423.

In step S425, the CPU 50A stores image data of the projection image after the correction in the external storage device 50D.

In step S426, the CPU 50A determines whether or not the value of i is a predetermined value $i_{max}$. That is, in this step, it is determined whether or not the correction of all projection images has been completed. The CPU 50A proceeds to step S427 in a case in which it is determined that the value of i is not $i_{max}$, and ends this routine in a case in which it is determined that the value of i is $i_{max}$.

In step S427, the CPU 50A increments the value of i by 1, and returns the process to step S422. Correction processing on each projection image corresponding to each emission angle is performed by repeatedly performing the processing from step S422 to step S425, and image data after the correction is stored in the external storage device 50D.

In the present embodiment, density values when the cumulative number of pixels in the case of counting pixels in the order of density values reaches 10% and 90% of the total number of pixels are made to match between projection images. However, the method of determining the density values to be matched with each other between the projection images can be appropriately changed.

(Modification Example 3)

The image correction section 56 may linearly convert the density value of each pixel of the projection image corresponding to the emission angle $\theta_i$ ($\theta_i \neq 0°$) so that the density value of the maximum frequency (peak density value) in the projection image corresponding to the emission angle of 0° approximately matches that in the projection image corresponding to the emission angle $\theta_i$ ($\theta_i \neq 0°$) in addition to the density values when the cumulative number of pixels in the case of counting pixels in the order of density values reaches, for example, 10% and 90% of the total number of pixels.

Figure 15:
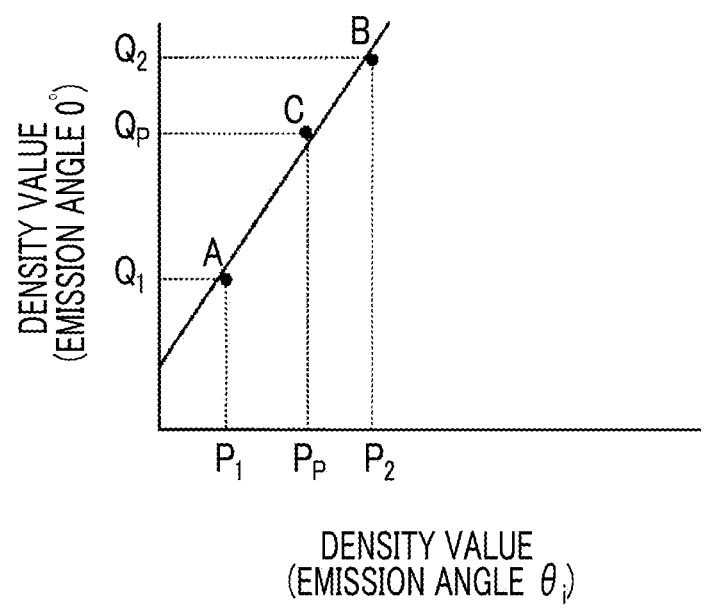
FIG. 15 is a diagram showing the concept of a density value conversion method according to another embodiment of the present invention.

FIG. 15 is a diagram showing the concept of the density value conversion method. In the graph shown in FIG. 15, the horizontal axis indicates the density value of the projection image corresponding to the emission angle $\theta_i$ ($\theta_i \neq 0°$), and the vertical axis indicates the density value of the projection image corresponding to the emission angle of 0°. $P_1$ is a density value when the cumulative number of pixels in the case of counting the pixels of the projection image corresponding to the emission angle $\theta_i$ ($\theta_i \neq 0°$) in the order of density values reaches 10% of the total number of pixels, and $P_2$ is a density value when the cumulative number of pixels in the case of counting the pixels of the projection image corresponding to the emission angle $\theta_i$ ($\theta_i \neq 0°$) in the order of density values reaches 90% of the total number of pixels. $P_P$ is a peak density value in the projection image corresponding to the emission angle $\theta_i$ ($\theta_i \neq 0°$). $Q_1$ is a density value when the cumulative number of pixels in the case of counting the pixels of the projection image corresponding to the emission angle of 0° in the order of density values reaches 10% of the total number of pixels, and $Q_2$ is a density value when the cumulative number of pixels in the case of counting the pixels of the projection image corresponding to the emission angle of 0° in the order of density values reaches 90% of the total number of pixels. $Q_P$ is a peak density value in the projection image corresponding to the emission angle of 0°.

It is possible to plot a point A based on the density values $P_1$ and $Q_1$, it is possible to plot a point B from the density values $P_2$ and $Q_2$, and it is possible to plot a point C based on the density values $P_P$ and $Q_P$. The image correction section 56 converts the density value of each projection image corresponding to the emission angle $\theta_i$ ($\theta_i \neq 0°$) so that the difference between the density values $P_1$ and $Q_1$, the difference between the density values $P_2$ and $Q_2$, and the difference between the density values $P_P$ and $Q_P$ are reduced. As the specific method, the following three methods can be exemplified.

As a first example, the image correction section 56 may derive a straight line whose distance from each of the points A to C is reduced using the least squares method, derive the conversion function shown in Equation (3) based on the straight line, and convert the density value of each projection image corresponding to the emission angle $\theta_i$ ($\theta_i \neq 0°$) based on the conversion function. According to this method, a value obtained by squaring the respective density value differences and taking the sum is minimized.

As a second example, the image correction section 56 may derive a straight line connecting two of the points A to C, derive the conversion function shown in Equation (3) based on the straight line, and convert the density value of each projection image corresponding to the emission angle $\theta_i$ ($\theta_i \neq 0°$) based on the conversion function. According to this method, a value obtained by taking the absolute values of the respective density value differences and taking the sum is minimized.

As a third example, the image correction section may derive a straight line whose distances from the points A to C are reduced using the least biquadratic method, derive the conversion function shown in Equation (3) based on the straight line, and convert the density value of each projection image corresponding to the emission angle $\theta_i$ ($\theta_i \neq 0°$) based on the conversion function. According to this method, a value obtained by quadruplicating the respective density value differences and taking the sum is minimized.

Even if the density value conversion is performed as described above, it is possible to reduce the density difference and the contrast difference between the projection images.

Figure 16:
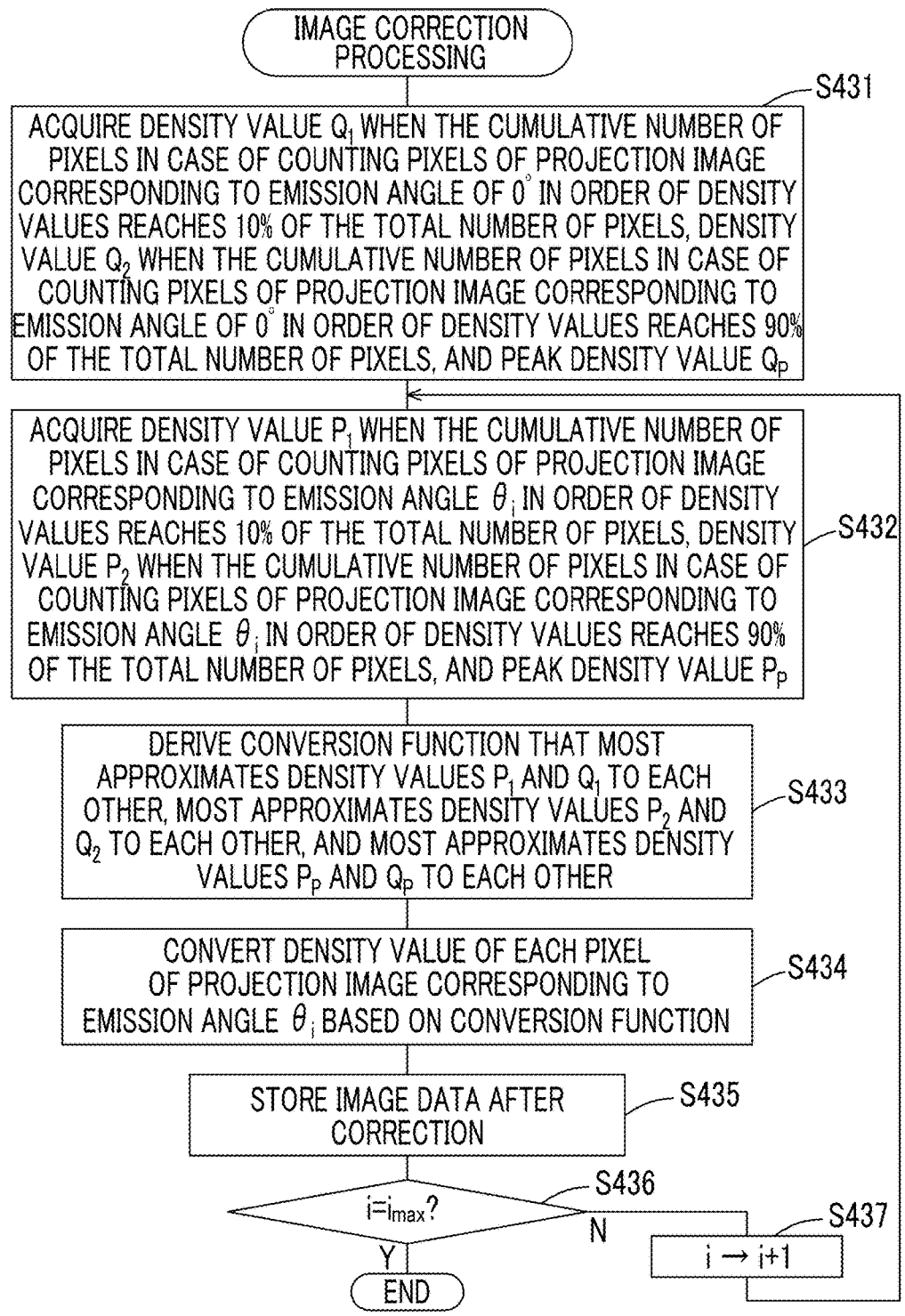
FIG. 16 is a flowchart showing the flow of processing in an image correction program according to another embodiment of the present invention.

FIG. 16 is a flowchart showing the flow of processing in an image correction program according to the modification example 3.

In step S431, the CPU 50A acquires the density value $Q_1$ when the cumulative number of pixels in the case of counting the pixels of the projection image corresponding to the emission angle of 0° in the order of density values reaches 10% of the total number of pixels, the density value $Q_2$ when the cumulative number of pixels in the case of counting the pixels of the projection image corresponding to the emission angle of 0° in the order of density values reaches 90% of the total number of pixels, and the peak density value $Q_P$.

In step S432, the CPU 50A acquires the density value $P_1$ when the cumulative number of pixels in the case of counting the pixels of the projection image corresponding to the emission angle $\theta_i$ ($\theta_i \neq 0°$) in the order of density values reaches 10% of the total number of pixels, the density value $P_2$ when the cumulative number of pixels in the case of counting the pixels of the projection image corresponding to the emission angle $\theta_i$ ($\theta_i \neq 0°$) in the order of density values reaches 90% of the total number of pixels, and the peak density value $P_P$.

In step S433, the CPU 50A derives a conversion function that most approximates the density value $P_1$ and the density value $Q_1$ to each other, most approximates the density value $P_2$ and the density value $Q_2$ to each other, and most approximates the density value $P_P$ and the density value $Q_P$ to each other. Specifically, the CPU 50A calculates a straight line whose distance from each of the points A, B, and C shown in FIG. 15 is the shortest using the least squares method, and calculates the gain a and the offset b of the conversion function expressed by Equation (3) from the calculated straight line.

In step S434, the CPU 50A corrects the density value and the contrast of the projection image by converting the density value in each pixel of the projection image corresponding to the emission angle $\theta_i$ ($\theta_i \neq 0°$) based on the conversion function derived in step S433.

In step S435, the CPU 50A stores image data of the projection image after the correction in the external storage device 50D.

In step S436, the CPU 50A determines whether or not the value of i is a predetermined value $i_{max}$. That is, in this step, it is determined whether or not the correction of all projection images has been completed. The CPU 50A proceeds to step S437 in a case in which it is determined that the value of i is not $i_{max}$, and ends this routine in a case in which it is determined that the value of i is $i_{max}$.

In step S437, the CPU 50A increments the value of i by 1, and returns the process to step S432. Correction processing on each projection image corresponding to each emission angle is performed by repeatedly performing the processing from step S432 to step S435, and image data after the correction is stored in the external storage device 50D.

In the present embodiment, density values when the cumulative number of pixels in the case of counting pixels in the order of density values reaches 10% and 90% of the total number of pixels and the peak density value are made to match between the projection images. However, the method of determining the density values to be approximately matched with each other between the images can be appropriately changed. For example, the peak density value may be replaced with the average density value. In addition, the density values when the cumulative number of pixels in the case of counting pixels in the order of density values reaches 10% and 90% of the total number of pixels may be replaced with a minimum density value and a maximum density value, respectively.

(Modification Example 4)

In each embodiment described above, both the gain a and the offset b in the linear conversion function expressed by Equation (3) are set to convert the density value. However, only the gain a or only the offset b may be set to convert the density value. For example, the density value of each pixel of the projection image corresponding to the emission angle $\theta_i$ ($\theta_i \neq 0°$) may be linearly converted by setting only the gain a based on Equation (4). In this case, the contrast of the projection image corresponding to the emission angle $\theta_i$ ($\theta_i \neq 0°$) can be brought close to the contrast of the projection image corresponding to the emission angle of 0°. In addition, for example, the density value of each pixel of the projection image corresponding to the emission angle $\theta_i$ ($\theta_i \neq 0°$) may be converted by setting only the offset b such that the average density value or the peak density value matches that in the projection image corresponding to the emission angle of 0°. In this case, since the brightness (average density value) of the entire projection image corresponding to the emission angle $\theta_i$ ($\theta_i \neq 0°$) can be brought close to the brightness (average density value) of the entire projection image corresponding to the emission angle of 0°, it is possible to achieve a certain effect on the improvement in the quality of the reconstructed tomographic image. Thus, the image correction section 56 can be configured to correct each projection image so that at least one of the contrast difference and the density value difference between a plurality of projection images is reduced.

Although the density value is converted using the linear conversion function expressed by Equation (3) in each embodiment described above, the density value may also be converted using a nonlinear conversion function. In addition, in each embodiment described above, image correction is performed so that the density value and the contrast of the projection image corresponding to the emission angle $\theta_i$ ($\theta_i \neq 0°$) match the density value and the contrast of the projection image corresponding to the emission angle of 0°. However, the density value and the contrast of each projection image may be made to match the density value and the contrast of a projection image other than the projection image corresponding to the emission angle of 0°.

[Second Embodiment]

A second embodiment of the present invention will be described below. The image correction section 56 according to the first embodiment described above performs image correction using the density histogram (that is, statistical data) of the projection image at each emission angle acquired by tomosynthesis imaging. In contrast, an image correction section 56 according to the second embodiment performs image correction using image data of a projection image at each emission angle.

Figure 17:
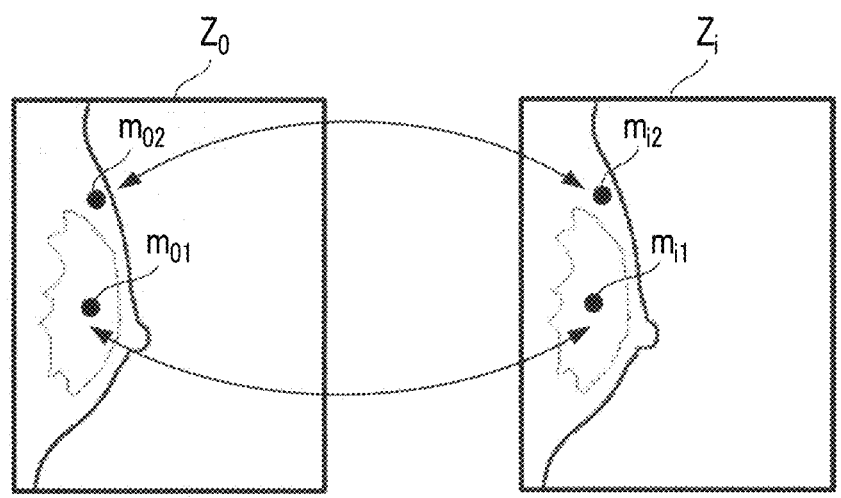
FIG. 17 is a diagram showing the outline of an image correction processing according to another embodiment of the present invention.

FIG. 17 is a diagram showing the outline of image correction processing in the image correction section 56 according to the second embodiment. The image correction section 56 specifies a mammary gland region and a fat region in a projection image $Z_0$ corresponding to the emission angle of 0° using a known image recognition technique (for example, the method described in "0038" to "0040" in JP2009-136376A). The image correction section 56 extracts a pixel group $m_{01}$ including, for example, arbitrary 3×3 pixels that is included in the specified mammary gland region and a pixel group $m_{02}$ including, for example, arbitrary 3×3 pixels that is included in the specified fat region, and acquires the average density value (average pixel value) of each of the extracted pixel groups $m_{01}$ and $m_{02}$. The image correction section 56 acquires the average density value of a pixel group $m_{i1}$ including 3×3 pixels, which corresponds to the pixel group $m_{01}$, and the average density value of a pixel group $m_{i2}$ including 3×3 pixels, which corresponds to the pixel group $m_{02}$, in a projection image $Z_i$ corresponding to the emission angle $\theta_i$ ($\theta_i \neq 0°$). Since the positions of the pixel groups $m_{01}$ and $m_{02}$ in the projection image $Z_0$ corresponding to the emission angle 0° are known, the positions of the pixel groups $m_{i1}$ and $m_{i2}$ corresponding to the pixel groups $m_{01}$ and $m_{02}$ in the projection image $Z_i$ corresponding to the emission angle $\theta_i$ ($\theta_i \neq 0°$) can be specified based on the positional relationship between the radiation source 26 and the radiation detector 36.

The image correction section 56 converts the density value of each pixel in the projection image $Z_i$ corresponding to the emission angle $\theta_i$ ($\theta_i \neq 0°$) so that the average density value of the pixel group $m_{i1}$ matches the average density value of the pixel group $m_{01}$ and the average density value of the pixel group $m_{i2}$ matches the average density value of the pixel group $m_{02}$. The density value of each pixel in the projection image $Z_i$ corresponding to the emission angle $\theta_i$ ($\theta_i \neq 0°$) can be converted using the conversion function expressed by Equation (3), for example. In this case, it is possible to derive a straight line connecting two points from the average density value of each of the pixel groups $m_{01}$, $m_{i1}$, $m_{02}$, and $m_{i2}$ according to the example shown in FIG. 13 and to calculate the gain a and the offset b in Equation (3) based on the derived straight line. The image correction section 56 converts the density value of each pixel of the projection image corresponding to the emission angle $\theta_i$ ($\theta_i \neq 0°$) based on the conversion function derived as described above. Even if the density value conversion is performed as described above, it is possible to reduce the density difference and the contrast difference between the projection images.

Figure 18:
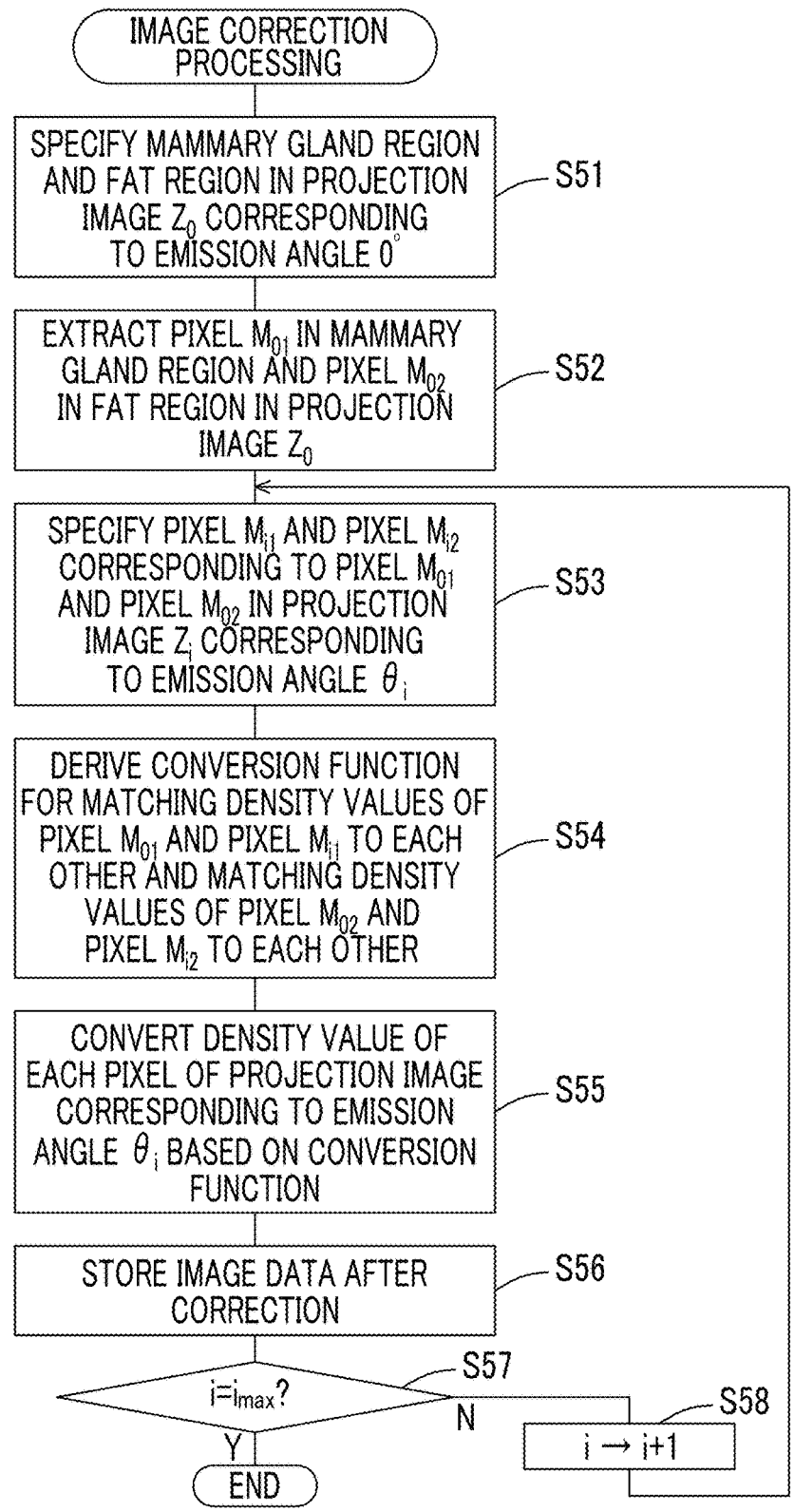
FIG. 18 is a flowchart showing the flow of processing in an image correction program according to another embodiment of the present invention.

FIG. 18 is a flowchart showing the flow of processing in an image correction program according to the second embodiment.

In step S51, the CPU 50A that functions as the image correction section 56 specifies a mammary gland region and a fat region in the projection image $Z_0$ corresponding to the emission angle 0° using a known image recognition technique.

In step S52, the CPU 50A extracts a pixel group $m_{01}$ including, for example, arbitrary 3×3 pixels in the mammary gland region in the projection image $Z_0$, and extracts a fat region $m_{02}$ including, for example, arbitrary 3×3 pixels in the fat region in the projection image $Z_0$. As a method of extracting arbitrary 3×3 pixels, for example, pixels corresponding to the density average value, the density median, or the center of gravity of each of the divided mammary gland region and fat region are extracted.

In step S53, the CPU 50A specifies the pixel group $m_{i1}$ at a position corresponding to the pixel group $m_{01}$ and the pixel group $m_{i2}$ at a position corresponding to the pixel group $m_{02}$ in the projection image Zi corresponding to emission angle $\theta_i$ ($\theta_i \neq 0°$) based on the positional relationship between the radiation source 26 and the radiation detector 36.

In step S54, the CPU 50A derives a conversion function for matching the average density value of the pixel group $m_{i1}$ with the average density value of the pixel group $m_{01}$ and matching the average density value of the pixel group $m_{i2}$ with the average density value of the pixel group $m_{02}$. Specifically, the CPU 50A derives the gain a and the offset b in Equation (3) based on the average density values of the pixel groups $m_{01}$, $m_{i1}$, $m_{02}$, and $m_{i2}$.

In step S55, the CPU 50A corrects the density value and the contrast of the projection image $Z_i$ by converting the density value in each pixel of the projection image $Z_i$ corresponding to the emission angle $\theta_i$ ($\theta_i \neq 0°$) based on the conversion function derived in step S54.

In step S56, the CPU 50A stores image data of the projection image $Z_i$ after the correction in the external storage device 50D.

In step S57, the CPU 50A determines whether or not the value of i is a predetermined value $i_{max}$. That is, in this step, it is determined whether or not the correction of all projection images has been completed. The CPU 50A proceeds to step S58 in a case in which it is determined that the value of i is not $i_{max}$, and ends this routine in a case in which it is determined that the value of i is $i_{max}$.

In step S58, the CPU 50A increments the value of i by 1, and returns the process to step S53. Correction processing on each projection image corresponding to each emission angle is performed by repeatedly performing the processing from step S53 to step S56, and image data after the correction is stored in the external storage device 50D.

Thus, by performing density value conversion so that the average density values of corresponding pixel groups in the projection image $Z_0$ corresponding to the emission angle of 0° and the projection image $Z_i$ corresponding to the emission angle $\theta_i$ ($\theta_i \neq 0°$) match each other, it is possible to further reduce the density value difference and the contrast difference between the images compared with the first embodiment in which density value conversion is performed using the statistical data of the density value. Therefore, the quality of a tomographic image that is reconstructed using a plurality of projection images can be improved more than in the related art.

In addition, since pixel groups having significantly different density values can be extracted by extracting a pixel group from each of the mammary gland region and the fat region that are different tissue of the breast M, it is possible to make the density value and the contrast uniform between the projection images more accurately. In addition, in the same manner as in the first embodiment, image correction is performed so that the density value and the contrast of the projection image corresponding to the emission angle $\theta_i$ ($\theta_i \neq 0°$) are brought close to the density value and the contrast of the projection image corresponding to the emission angle of 0°. Accordingly, it is possible to maintain the high contrast in the reconstructed tomographic image.

Although the average density value of a pixel group including 3×3 pixels is made to match between the projection images $Z_0$ and Zi in the present embodiment, the density value of one pixel extracted from each of the mammary gland region and the fat region or the average density value of a pixel group including pixels larger than 3×3 pixels may be made to match between the projection images $Z_0$ and Zi.

In the present embodiment, one pixel group is extracted from each of the mammary gland region and the fat region. However, two or more pixel groups may be extracted from each of the mammary gland region and the fat region. That is, the density value of the pixel of each projection image $Z_i$ is converted so that the difference between the average density value of each of at least three pixel groups in the projection image $Z_0$ corresponding to the emission angle of 0° and the average density value of each of pixel groups corresponding to the at least three pixel groups in the projection image $Z_i$ corresponding to the emission angle $\theta_i$ ($\theta_i \neq 0°$) is reduced. In this case, a straight line whose distance from each point is reduced may be derived using a least squares method or a least biquadratic method according to the example shown in FIG. 15, and the conversion function expressed by Equation (3) may be derived based on the straight line.

A mammary gland region and a fat region may be specified from the entire breast region using image processing in the projection image $Z_0$ corresponding to the emission angle of 0° and the projection image $Z_i$ corresponding to the emission angle $\theta_i$ ($\theta_i \neq 0°$), the average density value of the entire specified mammary gland region and the average density value of the entire specified fat region may be derived, and density value conversion may be performed so that the average density values in the projection images $Z_0$ and $Z_i$ match each other.

In the present embodiment, the CPU 50A specifies a mammary gland region and a fat region in the projection image $Z_0$ using the image recognition technique. However, the user may specify a mammary gland region and a fat region while checking the projection image $Z_0$ displayed on the monitor. In addition, the user may specify the pixel group $m_{01}$ of the mammary gland region and the pixel group $m_{02}$ of the fat region.

In addition, in the second embodiment, image correction is performed so that the density value and the contrast of the projection image corresponding to the emission angle $\theta_i$ ($\theta_i \neq 0°$) match the density value and the contrast of the projection image corresponding to the emission angle of 0°. However, the density value and the contrast of each projection image may be made to match the density value and the contrast of a projection image other than the projection image corresponding to the emission angle of 0°.

[Third Embodiment]

The image correction section 56 according to each of the first and second embodiments corrects the projection image corresponding to the emission angle $\theta_i$ ($\theta_i \neq 0°$) so that the density value and the contrast of the projection image corresponding to the emission angle $\theta_i$ ($\theta_i \neq 0°$) are brought close to the density value and the contrast of the projection image corresponding to the emission angle of 0°. The image correction section 56 according to the third embodiment has a standard density value that is set in advance for each of the mammary gland region and the fat region, and converts the density value of each pixel of each projection image so that the density values of specific pixels in the mammary gland region and the fat region in each projection image including the emission angle of 0° match the standard density value. That is, in the image correction according to the third embodiment, a projection image corresponding to the emission angle of 0° is also corrected.

Figure 19:
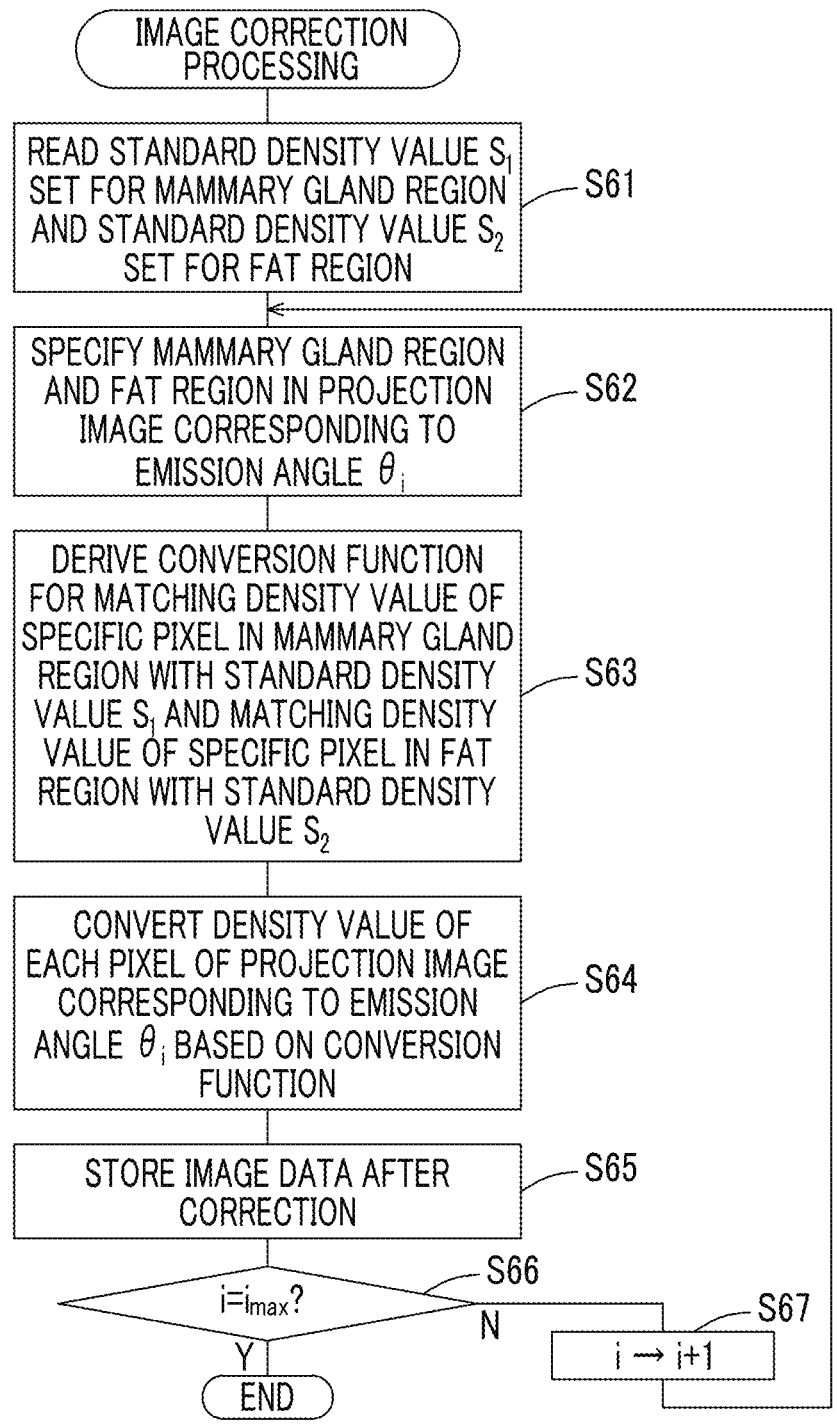
FIG. 19 is a flowchart showing the flow of processing in an image correction program according to another embodiment of the present invention.

FIG. 19 is a flowchart showing the flow of processing in an image correction program according to the third embodiment of the present invention.

In step S61, the CPU 50A that functions as the image correction section 56 reads a standard density value $S_1$, which is set in advance for the mammary gland region, and a standard density value $S_2$, which is set in advance for the fat region, from the ROM 50B.

In step S62, the CPU 50A specifies a mammary gland region and a fat region in the projection image corresponding to the emission angle $\theta_i$ (including the emission angle of 0°) using a known image recognition technique.

In step S63, the CPU 50A derives a conversion function for matching the density value of a specific pixel in the mammary gland region of the projection image with the standard density value $S_1$ and matching the density value of a specific pixel in the fat region with the standard density value $S_2$. Specifically, the CPU 50A derives a straight line connecting two points, according to the example shown in FIG. 13, from the density values of the specific pixels in the mammary gland region and the fat region of the projection image and the standard density values $S_1$ and $S_2$, and derives the gain a and the offset b in Equation (3) based on the derived straight line.

In step S64, the CPU 50A corrects the density value and the contrast of the projection image by converting the density value in each pixel of the projection image corresponding to the emission angle $\theta_i$ (including the emission angle of 0°) based on the conversion function derived in step S63.

In step S65, the CPU 50A stores image data of the projection image after the correction in the external storage device 50D.

In step S66, the CPU 50A determines whether or not the value of i is a predetermined value $i_{max}$. That is, in this step, it is determined whether or not the correction of all projection images has been completed. The CPU 50A proceeds to step S58 in a case in which it is determined that the value of i is not $i_{max}$, and ends this routine in a case in which it is determined that the value of i is $i_{max}$.

In step S67, the CPU 50A increments the value of i by 1, and returns the process to step S62. Correction processing on each projection image corresponding to each emission angle is performed by repeatedly performing the processing from step S62 to step S65, and image data after the correction is stored in the external storage device 50D.

Thus, even if the density value conversion is performed based on the standard density values $S_1$ and $S_2$ for each projection image including the emission angle of 0°, it is possible to reduce the density value difference and the contrast difference between the images. Therefore, the quality of a tomographic image that is reconstructed using a plurality of projection images can be improved more than in the related art.

In addition, according to the image correction of the present embodiment, even in a case in which the density value and the contrast of the projection image corresponding to the emission angle of 0° are not optimal, it is possible to set the appropriate density value and contrast since each projection image is corrected based on the standard density values $S_1$ and $S_2$.

Although the fixed values are used as the standard density values $S_1$ and $S_2$ in the present embodiment, the standard density values $S_1$ and $S_2$ may be changed according to the thickness of the breast M and the irradiation conditions, such as a tube voltage and a tube current. In this case, for example, a table showing the correspondence relationship between the thickness of the breast M and the irradiation conditions and the standard density values $S_1$ and $S_2$ is stored in the ROM 50B, and the standard density values $S_1$ and $S_2$ according to the thickness of the breast M and the irradiation conditions are derived by referring to the table.

[Fourth Embodiment]

In a fourth embodiment, processing for reducing the density difference and the contrast difference between images in the filtering process, which is performed before the back projection processing when reconstructing a tomographic image, is performed.

Figure 20:
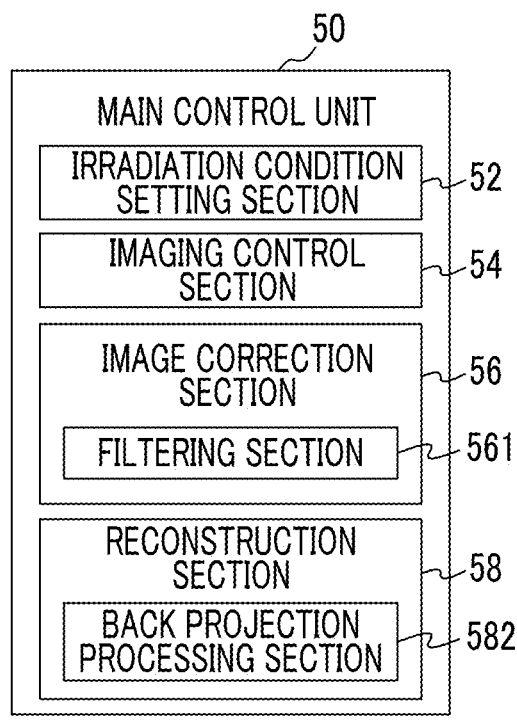
FIG. 20 is a functional block diagram showing the functional configuration of a main control unit according to another embodiment of the present invention.

FIG. 20 is a functional block diagram showing the functional configuration of the main control unit 50 according to the fourth embodiment. The main control unit 50 according to the fourth embodiment is different from those in the first to third embodiments in that the filtering section, which forms the reconstruction section 58 in the first to third embodiments, is included in the image correction section 56.

The basic function of a filtering section 561 according to the fourth embodiment is the same as that of the filtering section 581 (refer to FIG. 6) according to the first to third embodiments. That is, the filtering section 561 according to the present embodiment performs processing for superimposing a correction function for removing the blur in each projection image before performing back projection of the projection image. Specifically, the filtering section 561 converts the image data of each projection image into data in a frequency domain by performing a one-dimensional Fourier transform, and modifies the image data by multiplying the data in a frequency domain by a filter function.

Figure 21:
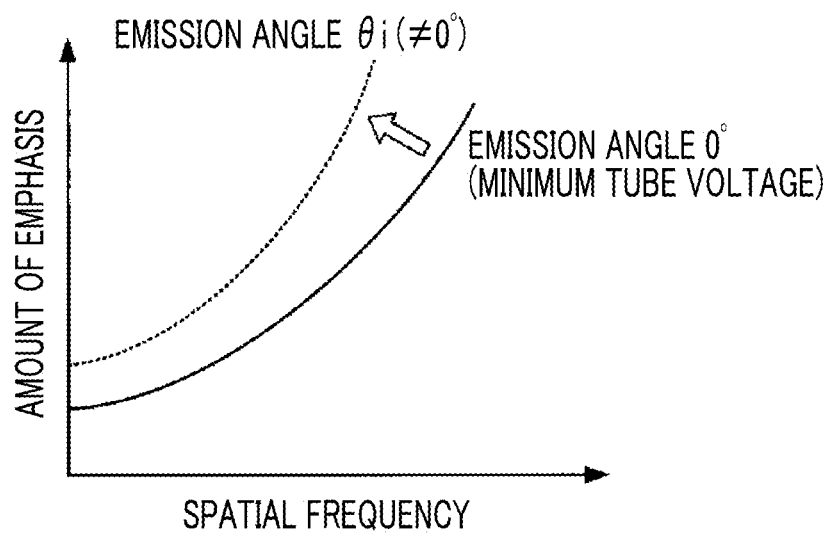
FIG. 21 is a diagram showing a filter function according to another embodiment of the present invention.

FIG. 21 is a diagram showing a filter function used in the filtering section 561. In the graph shown in FIG. 21, the horizontal axis indicates a spatial frequency, and the vertical axis indicates the amount of emphasis. As shown in FIG. 21, the filtering section 561 performs high frequency emphasis filtering processing, which is for increasing the amount of emphasis as the spatial frequency increases, on each projection image. By processing the projection image with the high frequency emphasis filter, it is possible to prevent the blur occurring in the image reconstructed by back projection. In addition, it is also possible to change the density value and the contrast of each projection image by changing the inclination or the intercept of the filter function.

The filtering section 561 according to the present embodiment performs filtering processing using a filter function that is different depending on the set value of the tube voltage (that is, depending on the emission angle of radiation), as shown in FIG. 21. Specifically, in the case of performing filtering processing on the projection image corresponding to the emission angle $\theta_i$ ($\theta_i \neq 0°$), the filtering section 581 uses a filter function having the larger amount of emphasis in each frequency band than in the case of performing filtering processing on the projection image corresponding to the emission angle of 0°. The filtering section 581 performs a high frequency emphasis processing on a projection image with a larger set value of tube voltage using a filter function having the larger amount of emphasis. By changing the amount of emphasis of the filter function according to the set value of the tube voltage as described above, it is possible to reduce the density value difference and the contrast difference between a plurality of projection images as in the first to third embodiments described above. Therefore, the quality of a tomographic image that is reconstructed using a plurality of projection images can be improved more than in the related art. In the filter function, the change in the amount of emphasis with respect to the spatial frequency may be linear, or may be nonlinear as shown in FIG. 21.

In each embodiment described above, the irradiation condition setting section 52, the imaging control section 54, the image correction section 56, and the reconstruction section 58 are realized by software. However, these may be realized by hardware, such as a semiconductor chip, or may be realized by combination of hardware and software.

The disclosure of Japanese Patent Application No. 2013-202061 is entirely incorporated in this specification by reference.

All documents, patent applications, and technical standards described in this specification are incorporated in this specification by reference to the same extent as in a case in which the incorporation of individual documents, patent applications, and technical standards by reference is described specifically and individually.

EXPLANATION OF REFERENCES

- 10: mammography device
- 26: radiation source
- 36: radiation detector
- 40: compression plate
- 50: main control unit
- 50A: CPU
- 50B: ROM
- 50C: RAM
- 50D: external storage device
- 52: irradiation condition setting section
- 54: imaging control section
- 56: image correction section
- 58: reconstruction section
- 561, 581: filtering section

What is claimed is:

1. A mammography device, comprising:
an x-ray radiation source that emits x-ray radiation to a breast at a plurality of different emission angles;
a condition setting unit that sets irradiation conditions corresponding to an emission angle of x-ray radiation emitted from the x-ray radiation source;
an image generation unit that generates a plurality of projection images corresponding to the plurality of emission angles by detecting x-ray radiation, which is emitted from the x-ray radiation source based on the irradiation conditions set by the condition setting unit and is transmitted through the breast;
a correction unit that corrects each projection image such that a difference between at least either contrasts or density values in the plurality of projection images is reduced; and
a reconstruction unit that reconstructs a tomographic image based on the plurality of projection images corrected by the correction unit,
wherein the condition setting unit increases a set value of a tube voltage in the x-ray radiation source as a transmission distance of x-ray radiation transmitted through the breast increases according to the emission angle of x-ray radiation, and
wherein the correction unit converts a density value of a projection image corresponding to each of other emission angles such that a density value of a first pixel group including at least one pixel in a projection image corresponding to a predetermined emission angle matches a density value of a pixel group corresponding to the first pixel group in the projection image corresponding to each of the other emission angles and a density value of a second pixel group including at least one pixel in the projection image corresponding to the predetermined emission angle matches a density value of a pixel group corresponding to the second pixel group in the projection image corresponding to each of the other emission angles.

2. The mammography device according to claim 1, wherein the first and second pixel groups are pixels extracted from different tissues in the breast.

3. The mammography device according to claim 1, wherein the predetermined emission angle is an emission angle at which the transmission distance of x-ray radiation transmitted through the breast is the shortest.

4. The mammography device according to claim 1, wherein the correction unit converts a density value of each pixel in each projection image by linear conversion.

5. A mammography device, comprising:
an x-ray radiation source that emits x-ray radiation to a breast at a plurality of different emission angles;
a condition setting unit that sets irradiation conditions corresponding to an emission angle of x-ray radiation emitted from the x-ray radiation source;
an image generation unit that generates a plurality of projection images corresponding to the plurality of emission angles by detecting x-ray radiation, which is emitted from the x-ray radiation source based on the irradiation conditions set by the condition setting unit and is transmitted through the breast;
a correction unit that corrects each projection image such that a difference between at least either contrasts or density values in the plurality of projection images is reduced; and
a reconstruction unit that reconstructs a tomographic image based on the plurality of projection images corrected by the correction unit,
wherein the condition setting unit increases a set value of a tube voltage in the x-ray radiation source as a transmission distance of x-ray radiation transmitted through the breast increases according to the emission angle of x-ray radiation, and
wherein the correction unit converts a density value of a projection image corresponding to each of other emission angles such that differences between density values of at least three pixel groups in a projection image corresponding to a predetermined emission angle and density values of pixel groups corresponding to the at least three pixel groups in the projection image corresponding to each of the other emission angles are reduced.

6. A mammography device, comprising:
an x-ray radiation source that emits x-ray radiation to a breast at a plurality of different emission angles;
a condition setting unit that sets irradiation conditions corresponding to an emission angle of x-ray radiation emitted from the x-rayg23 radiation source;
an image generation unit that generates a plurality of projection images corresponding to the plurality of emission angles by detecting x-ray radiation, which is emitted from the x-ray radiation source based on the irradiation conditions set by the condition setting unit and is transmitted through the breast;
a correction unit that corrects each projection image such that a difference between at least either contrasts or density values in the plurality of projection images is reduced; and
a reconstruction unit that reconstructs a tomographic image based on the plurality of projection images corrected by the correction unit,
wherein the condition setting unit increases a set value of a tube voltage in the x-ray radiation source as a transmission distance of x-ray radiation transmitted through the breast increases according to the emission angle of x-ray radiation, and
wherein the correction unit converts a density value of each of the plurality of projection images such that a density value of a first pixel in each of the plurality of projection images matches a first standard density value set for the first pixel and a density value of a second pixel in each of the plurality of projection images matches a second standard density value set for the second pixel.

7. A mammography device, comprising:
an x-ray radiation source that emits x-ray radiation to a breast at a plurality of different emission angles;
a condition setting unit that sets irradiation conditions corresponding to an emission angle of x-ray radiation emitted from the x-ray radiation source;
an image generation unit that generates a plurality of projection images corresponding to the plurality of emission angles by detecting x-ray radiation, which is emitted from the x-ray radiation source based on the irradiation conditions set by the condition setting unit and is transmitted through the breast;
a correction unit that corrects each projection image such that a difference between at least either contrasts or density values in the plurality of projection images is reduced; and
a reconstruction unit that reconstructs a tomographic image based on the plurality of projection images corrected by the correction unit,
wherein the correction unit converts image data of each of the plurality of projection images into data in a frequency domain by performing a Fourier transform, and performs filtering processing for multiplying the data in the frequency domain by a filter function of increasing the amount of emphasis in each frequency band as a transmission distance of x-ray radiation transmitted through the breast increases according to the emission angle of x-ray radiation.

8. The mammography device according to claim 7, wherein the condition setting unit increases a set value of a tube voltage in the x-ray radiation source as a transmission distance of x-ray radiation transmitted through the breast increases according to the emission angle of x-ray radiation.

9. A radiographic imaging method, comprising:
setting irradiation conditions corresponding to an emission angle of x-ray radiation emitted from an x-ray radiation source;
emitting x-ray radiation from the x-ray radiation source to a breast at a plurality of different emission angles based on the set irradiation conditions;
generating a plurality of projection images corresponding to the plurality of emission angles by detecting x-ray radiation, which is emitted from the x-ray radiation source and is transmitted through the breast;
correcting each projection image such that a difference between at least either contrasts or density values in the plurality of projection images is reduced; and
reconstructing a tomographic image based on the plurality of the corrected projection images,
wherein setting irradiation conditions includes increasing a set value of a tube voltage in the x-ray radiation source as a transmission distance of x-ray radiation transmitted through the breast increases according to the emission angle of x-ray radiation, and
wherein correcting each projection image includes converting a density value of a projection image corresponding to each of other emission angles such that differences between density values of at least three pixel groups in a projection image corresponding to a predetermined emission angle and density values of pixel groups corresponding to the at least three pixel groups in the projection image corresponding to each of the other emission angles are reduced.

* * * * *